(12) United States Patent
Shudo

(10) Patent No.: US 11,937,928 B2
(45) Date of Patent: Mar. 26, 2024

(54) EVALUATION APPARATUS, EVALUATION METHOD, AND EVALUATION PROGRAM

(71) Applicant: JVCKENWOOD Corporation, Yokohama (JP)

(72) Inventor: Katsuyuki Shudo, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 597 days.

(21) Appl. No.: 17/168,219

(22) Filed: Feb. 5, 2021

(65) Prior Publication Data

US 2021/0153795 A1    May 27, 2021

Related U.S. Application Data

(63) Continuation of application No. PCT/JP2019/021416, filed on May 29, 2019.

(30) Foreign Application Priority Data

Aug. 31, 2018    (JP) .................................. 2018-163114

(51) Int. Cl.
*A61B 3/14*    (2006.01)
*A61B 5/00*    (2006.01)
(Continued)

(52) U.S. Cl.
CPC .............. *A61B 5/163* (2017.08); *A61B 5/168* (2013.01); *A61B 5/742* (2013.01); *G06F 3/013* (2013.01); *G16H 50/20* (2018.01)

(58) Field of Classification Search
CPC ......... A61B 5/163; A61B 5/168; A61B 5/742; G06F 3/013; G16H 50/20
(Continued)

(56) References Cited

U.S. PATENT DOCUMENTS 6,243,076 B1 *   6/2001   Hatfield .................. G06F 3/038
                                                        715/977
2016/0106354 A1 *  4/2016   Shudo .................. A61B 3/0091
                                                        351/210
(Continued)

FOREIGN PATENT DOCUMENTS

EP        3202331        8/2017
JP      2011-083403      4/2011
(Continued)

OTHER PUBLICATIONS

Extended European Search Report for European Patent Application No. 19853433.1 dated Aug. 5, 2021.
(Continued)

*Primary Examiner* — Mahidere S Sahle
(74) *Attorney, Agent, or Firm* — Amin, Turocy & Watson, LLP

(57) ABSTRACT

An evaluation apparatus includes a display screen that displays an image; a gaze point detection unit that detects a position of a gaze point of a subject who observes the display screen, a display control unit that performs instruction display operation of displaying, on the display screen, a task target object to be gazed at by the subject and instruction information for instructing the subject to solve a task related to the task target object, a region setting unit that sets, on the display screen, a task region corresponding to the task target object and an instruction region corresponding to the instruction information, and a determination unit that determines whether the gaze point is present in the task region and the instruction region during an instruction display period in which the instruction display operation is performed on the basis of positional data of the gaze point.

4 Claims, 11 Drawing Sheets

(51) Int. Cl.
*A61B 5/16* (2006.01)
*G06F 3/01* (2006.01)
*G16H 50/20* (2018.01)

(58) Field of Classification Search
USPC ........................................................ 351/209
See application file for complete search history.

(56) References Cited

U.S. PATENT DOCUMENTS

2017/0188930 A1* 7/2017 Lahvis .................. A61B 5/168
2017/0224210 A1* 8/2017 Mori .................... A61B 5/7275

FOREIGN PATENT DOCUMENTS

| WO | 2014/164453 | 10/2014 |
| WO | 2014/208761 | 12/2014 |
| WO | 2016/040673 | 3/2016 |

OTHER PUBLICATIONS

International Search Report and Written Opinion for International Application No. PCT/JP2019/021416 dated Aug. 27, 2019, 11 pages.

* cited by examiner

US 11,937,928 B2

EVALUATION APPARATUS, EVALUATION METHOD, AND EVALUATION PROGRAM

CROSS-REFERENCE TO RELATED APPLICATION(S)

This application is a Continuation of PCT international application Ser. No. PCT/JP2019/021416 filed on May 29, 2019 which designates the United States, incorporated herein by reference, and which claims the benefit of priority from Japanese Patent Application No. 2018-163114, filed on Aug. 31, 2018, incorporated herein by reference.

BACKGROUND

1. Technical Field

The present disclosure relates to an evaluation apparatus, an evaluation method, and an evaluation program.

2. Description of the Related Art

In recent years, cognitive impairment and brain impairment tend to increase, and it is demanded to detect cognitive impairment and brain impairment early and to quantitatively evaluate severity of symptoms. It is known that symptoms of cognitive impairment and brain impairment affect cognitive ability. Therefore, it is common to evaluate a subject based on cognitive ability of the subject. For example, an apparatus that displays a plurality of kinds of numbers, instructs a subject to add the numbers to obtain an answer, and checks the answer provided by the subject has been proposed (for example, see Japanese Laid-open Patent Publication No. 2011-083403 A).

However, in the method of Japanese Laid-open Patent Publication No. 2011-083403 A or the like, the subject selects an answer by operating a touch panel or the like, so that it is difficult to perform verification including contingency and it is difficult to ensure high evaluation accuracy. Therefore, there is a need to evaluate cognitive impairment and brain impairment with high accuracy.

SUMMARY

It is an object of the present disclosure to at least partially solve the problems in the conventional technology.

An evaluation apparatus according to the present disclosure comprising: a display screen that displays an image; a gaze point detection unit that detects a position of a gaze point of a subject who observes the display screen; a display control unit that performs instruction display operation of displaying, on the display screen, a task target object to be gazed at by the subject and instruction information for instructing the subject to solve a task related to the task target object; a region setting unit that sets, on the display screen, a task region corresponding to the task target object and an instruction region corresponding to the instruction information; a determination unit that determines whether the gaze point is present in the task region and the instruction region during an instruction display period in which the instruction display operation is performed, on the basis of positional data of the gaze point; an arithmetic unit that calculates instruction movement course data indicating a course of movement of the gaze point during the instruction display period, on the basis of a determination result; and an evaluation unit that obtains evaluation data of the subject on the basis of the instruction movement course data.

An evaluation method according to the present disclosure comprising: displaying an image on a display screen; detecting a position of a gaze point of a subject who observes the display screen; performing instruction display operation of displaying, on the display screen, a task target object to be gazed at by the subject and instruction information for instructing the subject to solve a task related to the task target object; setting, on the display screen, a task region corresponding to the task target object and an instruction region corresponding to the instruction information; determining whether the gaze point is present in the task region and the instruction region during an instruction display period in which the instruction display operation is performed, on the basis of positional data of the gaze point; calculating instruction movement course data indicating a course of movement of the gaze point during the instruction display period, on the basis of a determination result; and obtaining evaluation data of the subject on the basis of the instruction movement course data.

A non-transitory computer readable recording medium storing therein an evaluation program according to the present disclosure that causes a computer to execute: a process of displaying an image on a display screen; a process of detecting a position of a gaze point of a subject who observes the display screen; a process of performing instruction display operation of displaying, on the display screen, a task target object to be gazed at by the subject and instruction information for instructing the subject to solve a task related to the task target object; a process of setting, on the display screen, a task region corresponding to the task target object and an instruction region corresponding to the instruction information; a process of determining whether the gaze point is present in the task region and the instruction region during an instruction display period in which the instruction display operation is performed, on the basis of positional data of the gaze point; a process of calculating instruction movement course data indicating a course of movement of the gaze point during the instruction display period, on the basis of a determination result; and a process of obtaining evaluation data of the subject on the basis of the instruction movement course data.

DETAILED DESCRIPTION OF THE PREFERRED EMBODIMENTS

Embodiments of an evaluation apparatus, an evaluation method, and an evaluation program according to the present disclosure will be described below based on the drawings. The present disclosure is not limited by the embodiments below. In addition, constituent elements described in the embodiments below include one that can be easily replaced by a person skilled in the art and one that is practically identical.

In the description below, a three-dimensional global coordinate system is set to describe positional relationships among components. A direction parallel to a first axis of a predetermined plane is referred to as an X-axis direction, a direction parallel to a second axis perpendicular to the first axis in the predetermined plane is referred to as a Y-axis direction, and a direction perpendicular to each of the first axis and the second axis is referred to as a Z-axis direction. The predetermined plane includes an XY plane.

Line-of-Sight Detection Apparatus

Figure 1:
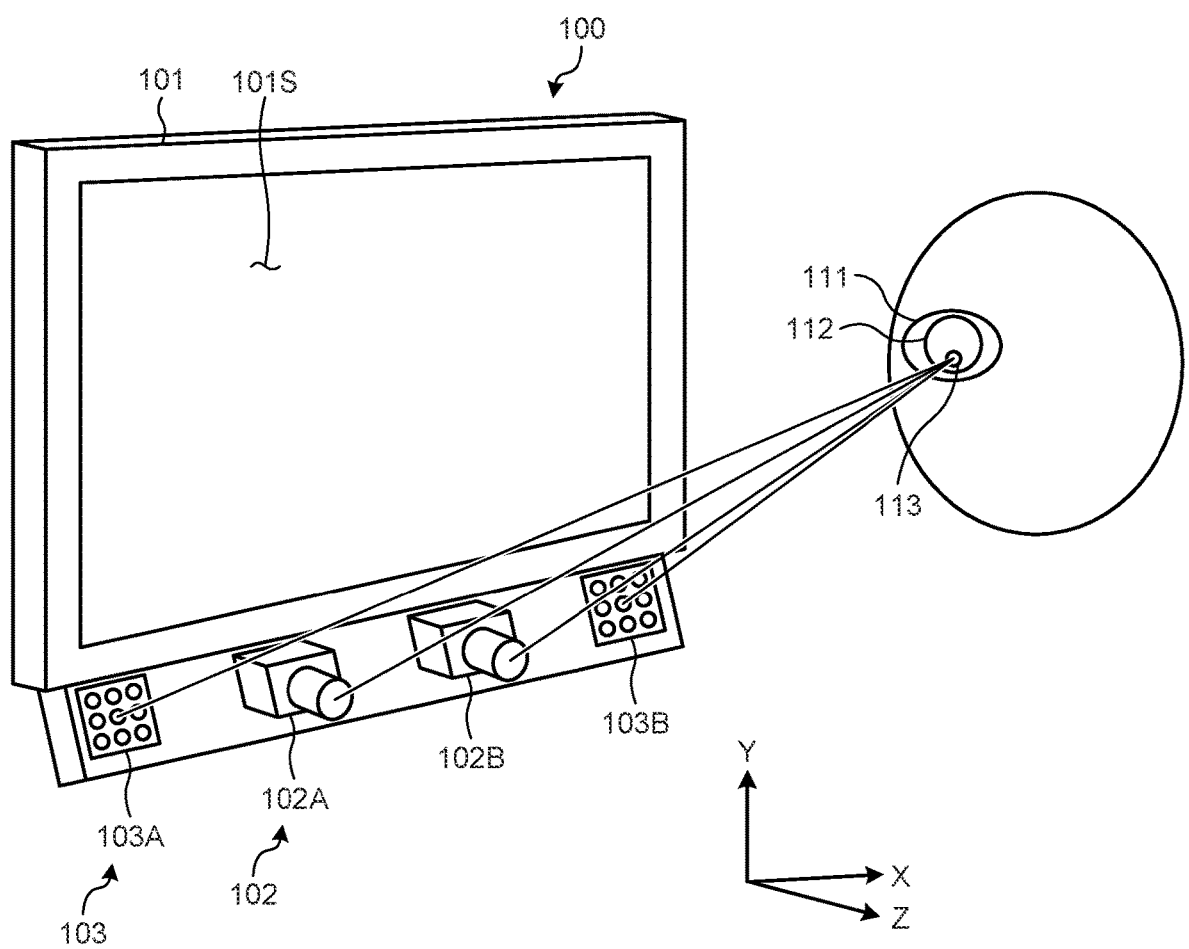
FIG. 1 is a perspective view schematically illustrating an example of a line-of-sight detection apparatus according to a present embodiment.

FIG. 1 is a perspective view schematically illustrating an example of a line-of-sight detection apparatus 100 according to a first embodiment. The line-of-sight detection apparatus 100 is used as an evaluation apparatus that evaluates cognitive impairment and brain impairment. As illustrated in FIG. 1, the line-of-sight detection apparatus 100 includes a display device 101, a stereo camera device 102, and a lighting device 103.

The display device 101 includes a flat panel display, such as a liquid crystal display (LCD) or an organic electroluminescence (EL) display (OLED). In the present embodiment, the display device 101 includes a display screen 101S. The display screen 101S displays an image. In the present embodiment, the display screen 101S displays, for example, an index for evaluating visual performance of a subject. The display screen 101S is substantially parallel to the XY plane. The X-axis direction corresponds to a horizontal direction of the display screen 101S, the Y-axis direction corresponds to a vertical direction of the display screen 101S, and the Z-axis direction corresponds to a depth direction perpendicular to the display screen 101S.

The stereo camera device 102 includes a first camera 102A and a second camera 102B. The stereo camera device 102 is arranged below the display screen 101S of the display device 101. The first camera 102A and the second camera 102B are arranged in the X-axis direction. The first camera 102A is arranged in the negative X direction relative to the second camera 102B. Each of the first camera 102A and the second camera 102B includes an infrared camera, an optical system capable of transmitting near-infrared light with a wavelength of 850 nanometers (nm) for example, and an imaging element capable of receiving the near-infrared light.

The lighting device 103 includes a first light source 103A and a second light source 103B. The lighting device 103 is arranged below the display screen 101S of the display device 101. The first light source 103A and the second light source 103B are arranged in the X-axis direction. The first light source 103A is arranged in the negative X direction relative to the first camera 102A. The second light source 103B is arranged in the positive X direction relative to the second camera 102B. Each of the first light source 103A and the second light source 103B includes a light emitting diode (LED) light source and is able to emit near-infrared light with a wavelength of 850 nm, for example. Meanwhile, the first light source 103A and the second light source 103B may be arranged between the first camera 102A and the second camera 102B.

The lighting device 103 emits near-infrared light as detection light and illuminates an eyeball 111 of the subject. The stereo camera device 102 captures an image of a part of the eyeball 111 (hereinafter, the part of the eyeball is also referred to as the "eyeball") by the second camera 102B when the eyeball 111 is irradiated with the detection light emitted from the first light source 103A, and captures an image of the eyeball 111 by the first camera 102A when the eyeball 111 is irradiated with the detection light emitted from the second light source 103B.

At least one of the first camera 102A and the second camera 102B outputs a frame synchronous signal. The first light source 103A and the second light source 103B output detection light based on the frame synchronous signal. The first camera 102A captures image data of the eyeball 111 when the eyeball 111 is irradiated with the detection light emitted from the second light source 103B. The second camera 102B captures image data of the eyeball 111 when the eyeball 111 is irradiated with the detection light emitted from the first light source 103A.

If the eyeball 111 is irradiated with the detection light, a part of the detection light is reflected by a pupil 112, and light from the pupil 112 enters the stereo camera device 102. Further, if the eyeball 111 is irradiated with the detection light, a corneal reflection image 113 that is a virtual image of a cornea is formed on the eyeball 111, and light from the corneal reflection image 113 enters the stereo camera device 102.

By appropriately setting the relative position between the first camera 102A/the second camera 102B and the first light source 103A/the second light source 103B, intensity of light that enters from the pupil 112 to the stereo camera device 102 is reduced, and intensity of light that enters from the corneal reflection image 113 to the stereo camera device 102 is increased. In other words, an image of the pupil 112 captured by the stereo camera device 102 has low luminance, and an image of the corneal reflection image 113 has high luminance. The stereo camera device 102 is able to detect a position of the pupil 112 and a position of the corneal reflection image 113 on the basis of the luminance of the captured image.

Figure 2:
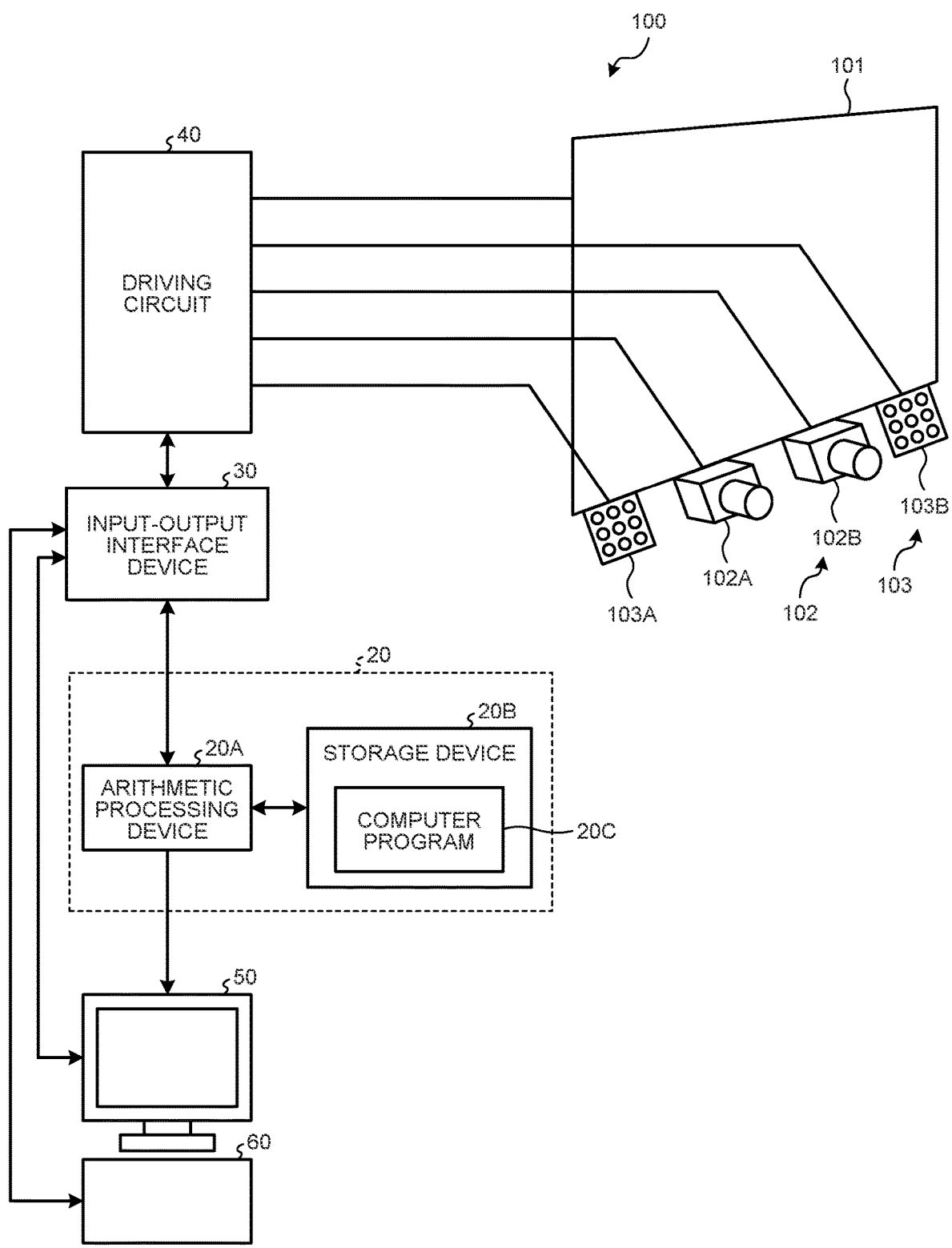
FIG. 2 is a diagram illustrating an example of a hardware configuration of the line-of-sight detection apparatus according to the present embodiment.

FIG. 2 is a diagram illustrating an example of a hardware configuration of the line-of-sight detection apparatus 100 according to the present embodiment. As illustrated in FIG. 2, the line-of-sight detection apparatus 100 includes the display device 101, the stereo camera device 102, the lighting device 103, a computer system 20, an input-output interface device 30, a driving circuit 40, an output device 50, and an input device 60.

The computer system 20, the driving circuit 40, the output device 50, and the input device 60 perform data communication via the input-output interface device 30. The computer system 20 includes an arithmetic processing device 20A and a storage device 20B. The arithmetic processing device 20A includes a microprocessor, such as a central processing unit (CPU). The storage device 20B includes a memory, such as a read only memory (ROM) and a random access memory (RAM), or a storage. The arithmetic processing device 20A performs an arithmetic process in accordance with a computer program 20C that is stored in the storage device 20B.

The driving circuit 40 generates a driving signal and outputs the driving signal to the display device 101, the stereo camera device 102, and the lighting device 103. Further, the driving circuit 40 supplies image data of the eyeball 111 that is captured by the stereo camera device 102 to the computer system 20 via the input-output interface device 30.

The output device 50 includes a display device, such as a flat panel display. The output device 50 may include a printing device. The input device 60 generates input data by being operated. The input device 60 includes a keyboard or a mouse for a computer system. The input device 60 may include a touch sensor that is arranged on a display screen of the output device 50 that serves as a display device.

In the present embodiment, the display device 101 and the computer system 20 are separated devices. However, the display device 101 and the computer system 20 may be integrated. For example, if the line-of-sight detection apparatus 100 includes a tablet personal computer, the computer system 20, the input-output interface device 30, the driving circuit 40, and the display device 101 may be mounted on the tablet personal computer.

Figure 3:
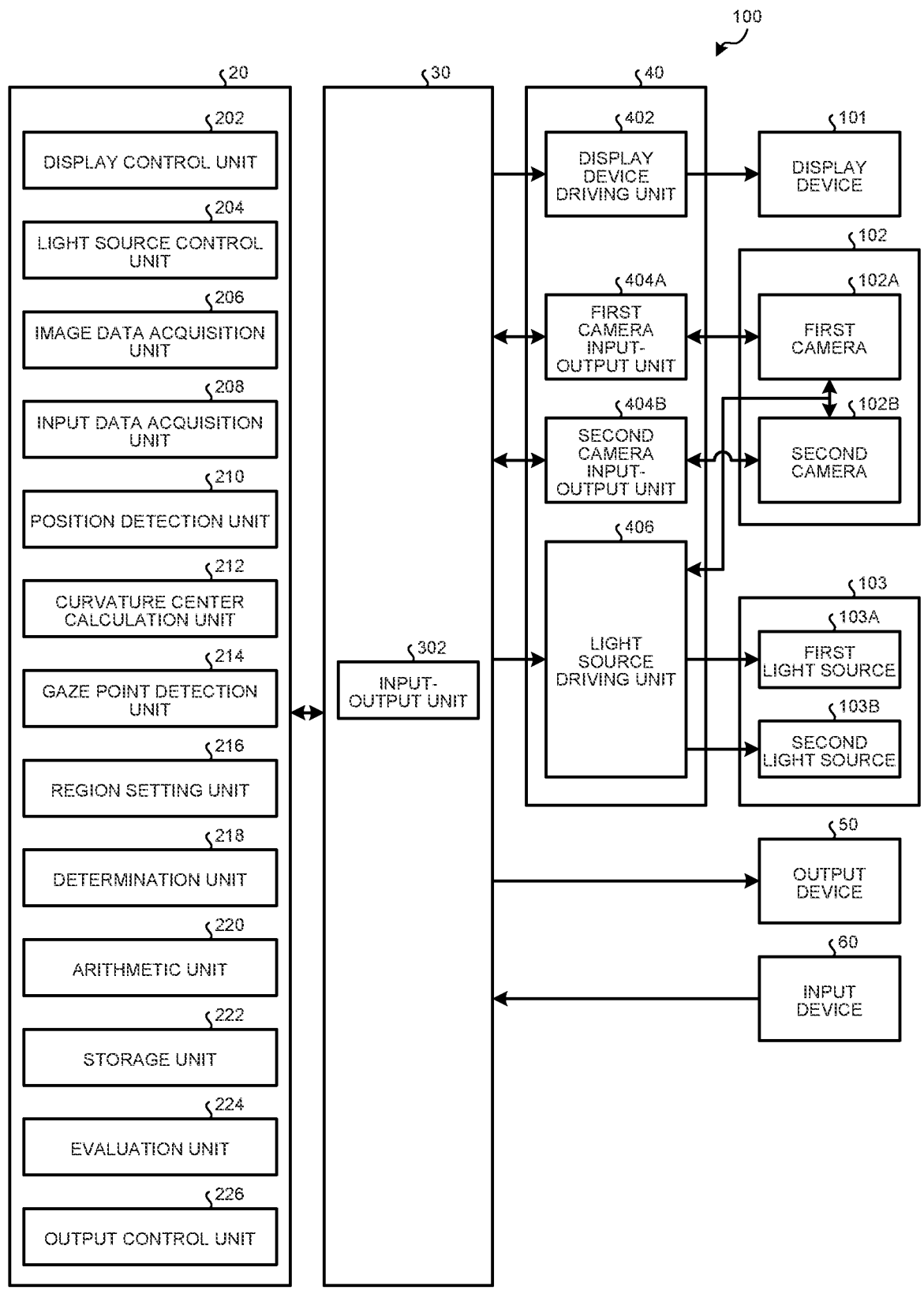
FIG. 3 is a functional block diagram illustrating an example of the line-of-sight detection apparatus according to the present embodiment.

FIG. 3 is a functional block diagram illustrating an example of the line-of-sight detection apparatus 100 according to the present embodiment. As illustrated in FIG. 3, the input-output interface device 30 includes an input-output unit 302. The driving circuit 40 includes a display device driving unit 402 that generates a driving signal for driving the display device 101 and outputs the driving signal to the display device 101, a first camera input-output unit 404A that generates a driving signal for driving the first camera 102A and outputs the driving signal to the first camera 102A, a second camera input-output unit 404B that generates a driving signal for driving the second camera 102B and outputs the driving signal to the second camera 102B, and a light source driving unit 406 that generates a driving signal for driving the first light source 103A and the second light source 103B and outputs the driving signal to the first light source 103A and the second light source 103B. Further, the first camera input-output unit 404A supplies image data of the eyeball 111 that is captured by the first camera 102A to the computer system 20 via the input-output unit 302. The second camera input-output unit 404B supplies image data of the eyeball 111 that is captured by the second camera 102B to the computer system 20 via the input-output unit 302.

The computer system 20 controls the line-of-sight detection apparatus 100. The computer system 20 includes a display control unit 202, a light source control unit 204, an image data acquisition unit 206, an input data acquisition unit 208, a position detection unit 210, a curvature center calculation unit 212, a gaze point detection unit 214, a region setting unit 216, a determination unit 218, an arithmetic unit 220, a storage unit 222, an evaluation unit 224, and an output control unit 226. Functions of the computer system 20 are implemented by the arithmetic processing device 20A and the storage device 20B.

The display control unit 202 performs instruction display operation of displaying, on the display screen 101S, a task target object that is to be gazed at by a subject, and instruction information for instructing the subject to solve a task related to the task target object. In the instruction display operation, the display control unit 202 displays, on the display screen, the instruction information including information for giving an instruction to gaze at a target object that is a correct answer for the task from among a plurality of target objects that are to be displayed on the display screen 101S after the instruction display operation. After the instruction display operation, the display control unit 202 performs target display operation of displaying, as a plurality of target objects, a specific target object that is a correct answer for the instruction information and comparison target objects that are different from the specific target object on the display screen 101S.

The instruction information includes characters, figures, and the like that are displayable on the display screen 101S. Examples of the task include a task for instructing the subject to memorize a task target object and select the same target object as the memorized task target object. The instruction information, the task target object, the specific target object, and the comparison target objects as described above are included in, for example, an evaluation video or an evaluation image that is to be viewed by the subject. The display control unit 202 displays the evaluation video or the evaluation image as described above on the display screen 101S. Meanwhile, the instruction information is not limited to a sentence form using characters, or the like. The instruction information may be in a certain form that does not use characters, such as a combination of figures, as long as it is possible to notify the subject of the task.

The light source control unit 204 controls the light source driving unit 406, and controls operation states of the first light source 103A and the second light source 103B. The light source control unit 204 controls the first light source 103A and the second light source 103B such that the first light source 103A and the second light source 103B emit detection light at different timings.

The image data acquisition unit 206 acquires the image data of the eyeball 111 of the subject that is captured by the stereo camera device 102 including the first camera 102A and the second camera 102B, from the stereo camera device 102 via the input-output unit 302.

The input data acquisition unit 208 acquires the input data that is generated through operation of the input device 60, from the input device 60 via the input-output unit 302.

The position detection unit 210 detects positional data of a pupil center on the basis of the image data of the eyeball 111 acquired by the image data acquisition unit 206. Further, the position detection unit 210 detects positional data of a corneal reflection center on the basis of the image data of the eyeball 111 acquired by the image data acquisition unit 206. The pupil center is a center of the pupil 112. The corneal reflection center is a center of the corneal reflection image 113. The position detection unit 210 detects the positional data of the pupil center and the positional data of the corneal reflection center for each of the right and left eyeballs 111 of the subject.

The curvature center calculation unit 212 calculates positional data of a corneal curvature center of the eyeball 111 on the basis of the image data of the eyeball 111 acquired by the image data acquisition unit 206.

The gaze point detection unit 214 detects positional data of a gaze point of the subject on the basis of the image data of the eyeball 111 acquired by the image data acquisition unit 206. In the present embodiment, the positional data of the gaze point indicates positional data of an intersection point between a line-of-sight vector of the subject that is defined by the three-dimensional global coordinate system and the display screen 101S of the display device 101. The gaze point detection unit 214 detects a line-of-sight vector of each of the right and left eyeballs 111 of the subject on the basis of the positional data of the pupil center and the positional data of the corneal curvature center that are acquired from the image data of the eyeball 111. After detection of the line-of-sight vector, the gaze point detection unit 214 detects the positional data of the gaze point that indicates the intersection point between the line-of-sight vector and the display screen 101S.

The region setting unit 216 sets a task region corresponding to the task target object and an instruction region corresponding to the instruction information on the display screen 101S during an instruction display period in which the instruction display operation is performed. Further, the region setting unit 216 sets a specific region corresponding to the specific target object and comparison regions corresponding to the comparison target objects on the display screen 101S during a target display period in which the target display operation is performed.

The determination unit 218 determines whether the gaze point is present in each of the task region and the instruction region during the instruction display period on the basis of positional data of a viewpoint, and outputs determination data. Further, the determination unit 218 determines whether the gaze point is present in each of the specific region and the comparison regions during the target display period on the basis of the positional data of the viewpoint, and outputs determination data. The determination unit 218 determines whether the gaze point is present in the specific region and the comparison regions at a constant time interval, for example. The constant time interval may be set to, for example, a cycle of the frame synchronous signal (for example, every 20 milliseconds (msec)) that is output from the first camera 102A and the second camera 102B.

The arithmetic unit 220 calculates instruction movement course data that indicates a course of movement of the gaze point during the instruction display period, on the basis of the determination data of the determination unit 218. Further, the arithmetic unit 220 calculates target movement course data that indicates a course of movement of the gaze point during the target display period, on the basis of the determination data of the determination unit 218.

The instruction movement course data includes first presence time data indicating a presence time in which the gaze point is present in the task region during the instruction display period, second presence time data indicating a presence time in which the gaze point is present in the instruction region during the instruction display period, instruction arrival time data indicating a time period from a start time of the instruction display period to an arrival time at which the gaze point arrives at the task region, and instruction movement frequency data indicating the number of times of movement of the position of the gaze point between the task region and the instruction region.

The target movement course data includes target arrival time data indicating a time period from a start time of the target display period to an arrival time at which the gaze point arrives at the specific region, target movement frequency data indicating the number of times of movement of the position of the gaze point among a plurality of comparison regions before the gaze point first arrives at the specific region, target presence time data indicating a presence time in which the gaze point is present in the specific region during a display period, and final region data indicating a region in which the gaze point is finally located among the specific region and the comparison regions during a display time.

Meanwhile, the arithmetic unit 220 includes a management timer for managing a video replay time, and a detection timer T1 for detecting an elapsed time since start of display of the video on the display screen 101S. The arithmetic unit 220 includes a counter that counts the number of times the gaze point is determined as being present in the specific region.

The evaluation unit 224 obtains evaluation data of the subject on the basis of the instruction movement course data. Further, the evaluation unit 224 is able to obtain the evaluation data of the subject on the basis of the instruction movement course data and the target movement course data. The evaluation data includes data for evaluating whether the subject is able to gaze at the task target object and the instruction information that are displayed on the display screen 101S in the instruction display operation. Further, the evaluation data includes data for evaluating whether the subject is able to gaze at the specific target object and the comparison target objects that are displayed on the display screen 101S in the target display operation.

The storage unit 222 stores therein the determination data, the instruction movement course data (the first presence time data, the second presence time data, the instruction arrival time data, and the instruction movement frequency data), the target movement course data (the target presence time data, the target movement frequency data, the final region data, and the target arrival time data), and the evaluation data as described above. Further, the storage unit 222 stores therein an evaluation program that causes a computer to execute a process of displaying an image on the display screen 101S, a process of detecting the position of the gaze point of the subject who observes the display screen 101S, a process of performing the instruction display operation of displaying, on the display screen 101S, a task target object to be gazed at by the subject and the instruction information for instructing the subject to solve a task related to the task target object, a process of setting the task region corresponding to the task target object and the instruction region corresponding to the instruction information on the display screen 101S, a process of determining, on the basis of positional data of the gaze point, whether the gaze point is present in each of the task region and the instruction region during the instruction display period in which the instruction display operation is performed, a process of calculating the instruction movement course data indicating the course of movement of the gaze point during the instruction display period on the basis of a determination result, and a process of obtaining the evaluation data of the subject on the basis of the instruction movement course data.

The output control unit 226 outputs data to at least one of the display device 101 and the output device 50.

Figure 4:
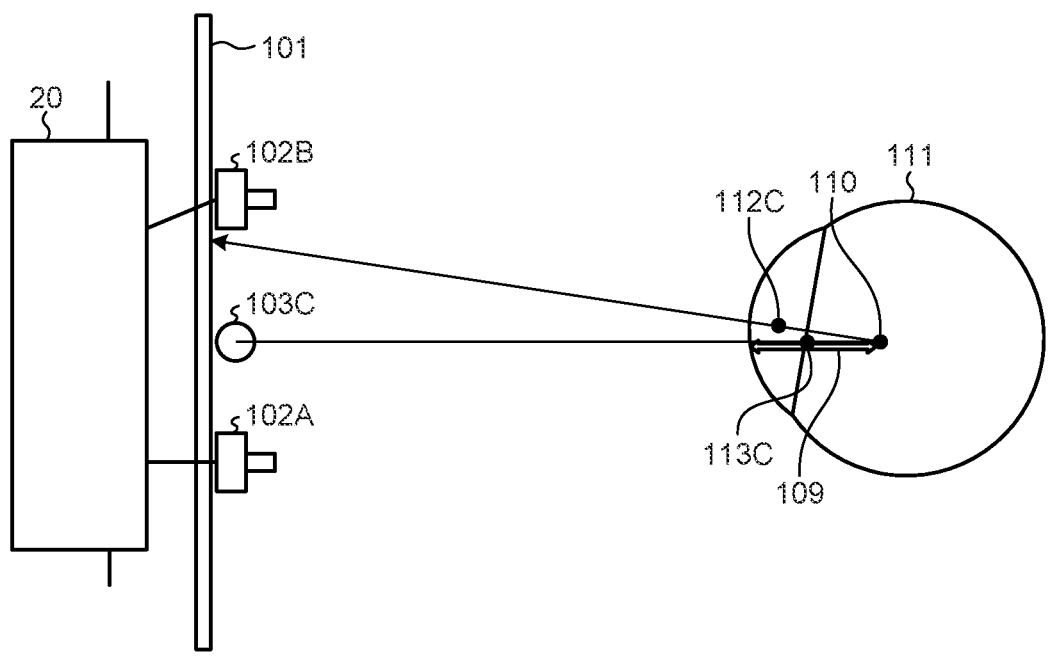
FIG. 4 is a schematic diagram for explaining a method of calculating positional data of a corneal curvature center according to the present embodiment.
Figure 5:
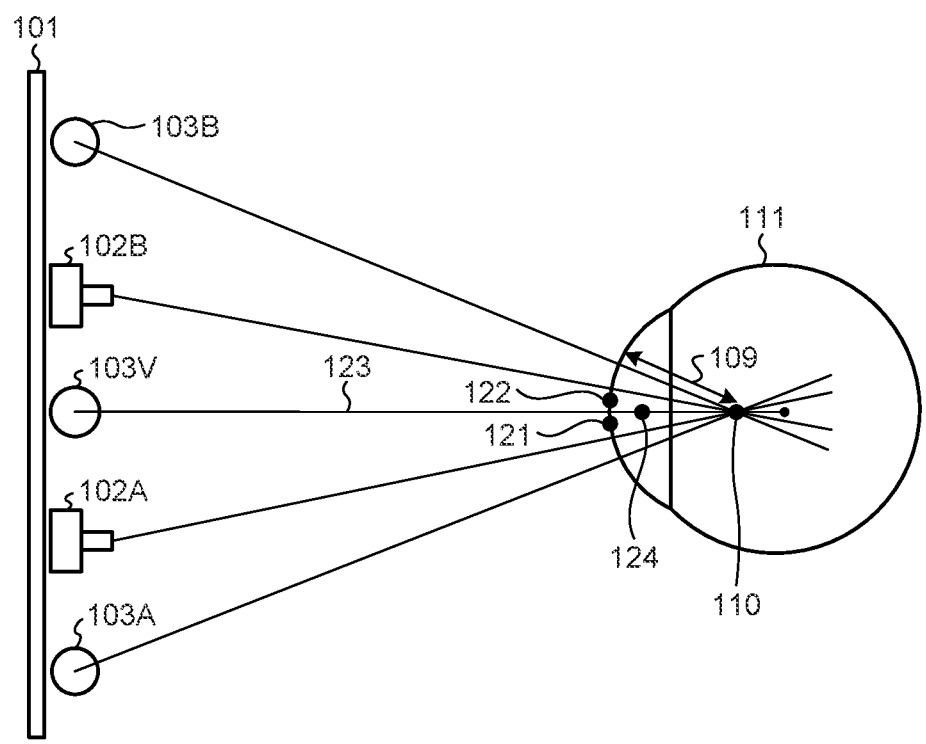
FIG. 5 is a schematic diagram for explaining the method of calculating the positional data of the corneal curvature center according to the present embodiment.

An overview of a process performed by the curvature center calculation unit 212 according to the present embodiment will be described below. The curvature center calculation unit 212 calculates the positional data of the corneal curvature center of the eyeball 111 on the basis of the image data of the eyeball 111. FIG. 4 and FIG. 5 are schematic diagrams for explaining a method of calculating positional data of a corneal curvature center 110 according to the present embodiment. FIG. 4 illustrates an example in which the eyeball 111 is illuminated by a single light source 103C. FIG. 5 illustrates an example in which the eyeball 111 is illuminated by the first light source 103A and the second light source 103B.

First, the example illustrated in FIG. 4 will be explained. The light source 103C is arranged between the first camera 102A and the second camera 102B. A pupil center 112C is the center of the pupil 112. A corneal reflection center 113C is the center of the corneal reflection image 113. In FIG. 4, the pupil center 112C indicates a pupil center that is obtained when the eyeball 111 is illuminated by the single light source 103C. The corneal reflection center 113C indicates a corneal reflection center that is obtained when the eyeball 111 is illuminated by the single light source 103C. The corneal reflection center 113C is located on a straight line that connects the light source 103C and the corneal curvature center 110. The corneal reflection center 113C is located at an intermediate point between a corneal surface and the corneal curvature center 110. A corneal curvature radius 109 is a distance between the corneal surface and the corneal curvature center 110. Positional data of the corneal reflection center 113C is detected by the stereo camera device 102. The corneal curvature center 110 is located on a straight line that connects the light source 103C and the corneal reflection center 113C. The curvature center calculation unit 212 calculates, as the positional data of the corneal curvature center 110, positional data for which a distance from the corneal reflection center 113C on the straight line is equal to a predetermined value. The predetermined value is a value that is determined in advance from a curvature radius value of a general cornea or the like, and stored in the storage unit 222.

Next, the example illustrated in FIG. 5 will be described. In the present embodiment, the first camera 102A/the second light source 103B and the second camera 102B/the first light source 103A are arranged at bilaterally symmetrical positions with respect to a straight line that passes through an intermediate position between the first camera 102A and the second camera 102B. It is possible to assume that a virtual light source 103V is present at the intermediate position between the first camera 102A and the second camera 102B. A corneal reflection center 121 indicates a corneal reflection center in an image that is obtained by capturing the eyeball 111 by the second camera 102B. A corneal reflection center 122 indicates a corneal reflection center in an image that is obtained by capturing the eyeball 111 by the first camera 102A. A corneal reflection center 124 indicates a corneal reflection center corresponding to the virtual light source 103V. Positional data of the corneal reflection center 124 is calculated based on the positional data of the corneal reflection center 121 and the positional data of the corneal reflection center 122 that are captured by the stereo camera device 102. The stereo camera device 102 detects the positional data of the corneal reflection center 121 and the positional data of the corneal reflection center 122 in a three-dimensional local coordinate system that is defined in the stereo camera device 102. Camera calibration using a stereo calibration method is performed in advance on the stereo camera device 102, and a transformation parameter for transforming the three-dimensional local coordinate system of the stereo camera device 102 into the three-dimensional global coordinate system is calculated. The transformation parameter is stored in the storage unit 222. The curvature center calculation unit 212 transforms the positional data of the corneal reflection center 121 and the positional data of the corneal reflection center 122, which are captured by the stereo camera device 102, into pieces of positional data in the three-dimensional global coordinate system by using the transformation parameter. The curvature center calculation unit 212 calculates the positional data of the corneal reflection center 124 in the three-dimensional global coordinate system, on the basis of the positional data of the corneal reflection center 121 and the positional data of the corneal reflection center 122 that are defined in the three-dimensional global coordinate system. The corneal curvature center 110 is located on a straight line that connects the virtual light source 103V and the corneal reflection center 124. The curvature center calculation unit 212 calculates, as the positional data of the corneal curvature center 110, positional data for which a distance from the corneal reflection center 124 on a straight line 123 is equal to a predetermined value. The predetermined value is a value that is determined in advance from a curvature radius value of a general cornea or the like, and stored in the storage unit 222.

As described above, even if the two light sources are provided, the corneal curvature center 110 is calculated by the same method as the method that is adopted when the single light source is provided.

The corneal curvature radius 109 is a distance between the corneal surface and the corneal curvature center 110. Therefore, the corneal curvature radius 109 is calculated by calculating positional data of the corneal surface and the positional data of the corneal curvature center 110.

Figure 6:
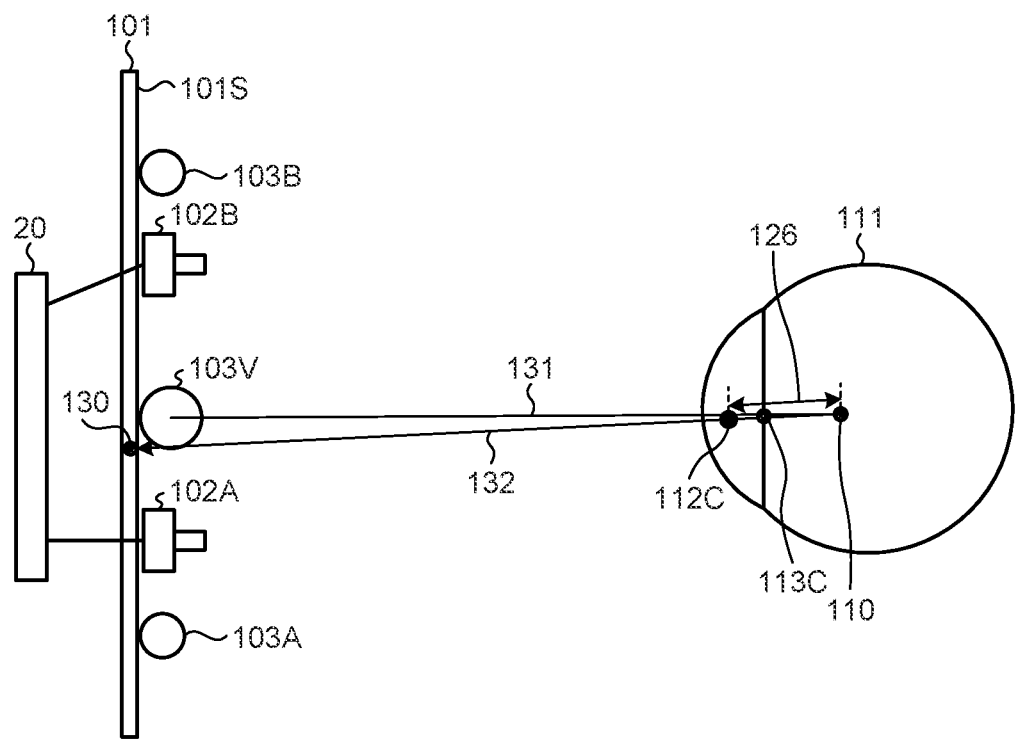
FIG. 6 is a schematic diagram for explaining an example of a calibration process according to the present embodiment.

Next, an example of the line-of-sight detection method according to the present embodiment will be described. FIG. 6 is a schematic diagram for explaining an example of a calibration process according to the present embodiment. In the calibration process, a target position 130 is set so as to be gazed at by the subject. The target position 130 is defined in the three-dimensional global coordinate system. In the present embodiment, the target position 130 is set at a central position of the display screen 101S of the display device 101, for example. Meanwhile, the target position 130 may be set at a position of an end portion of the display screen 101S. The output control unit 226 displays a target image at the set target position 130. A straight line 131 is a straight line that connects the virtual light source 103V and the corneal reflection center 113C. A straight line 132 is a straight line that connects the target position 130 and the pupil center 112C. The corneal curvature center 110 is an intersection point between the straight line 131 and the straight line 132. The curvature center calculation unit 212 is able to calculate the positional data of the corneal curvature center 110 on the basis of positional data of the virtual light source 103V, positional data of the target position 130, positional data of the pupil center 112C, and the positional data of the corneal reflection center 113C.

Figure 7:
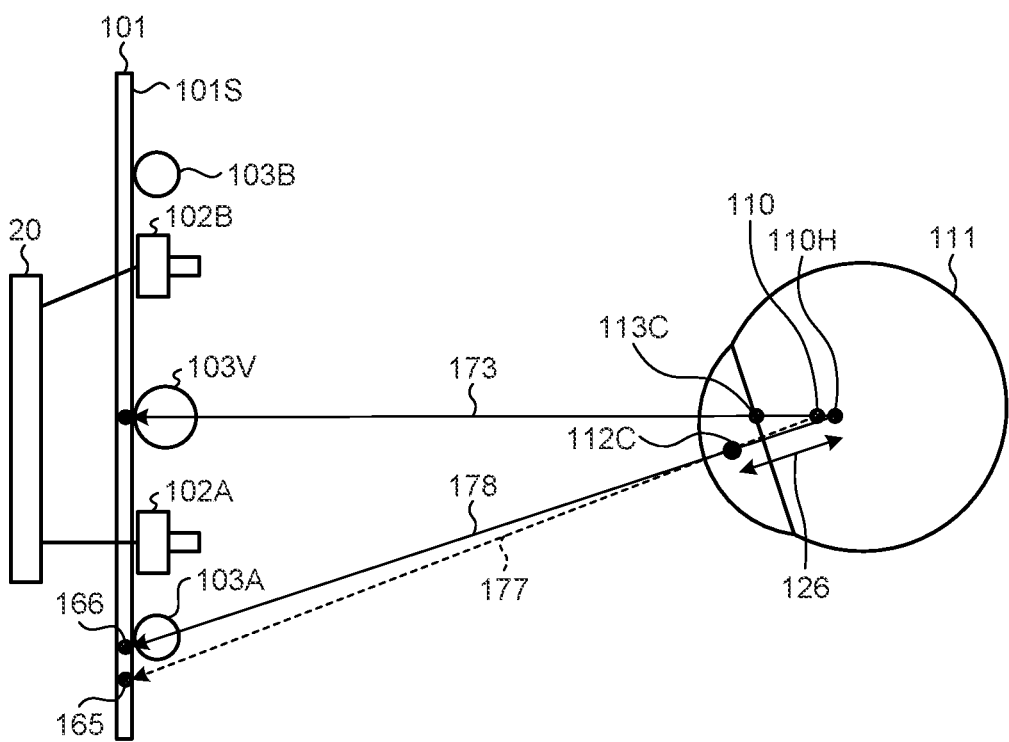
FIG. 7 is a schematic diagram for explaining an example of a gaze point detection process according to the present embodiment.

A gaze point detection process will be described below. The gaze point detection process is performed after the calibration process. The gaze point detection unit 214 calculates a line-of-sight vector of the subject and the positional data of the gaze point on the basis of the image data of the eyeball 111. FIG. 7 is a schematic diagram for explaining an example of the gaze point detection process according to the present embodiment. In FIG. 7, a gaze point 165 indicates a gaze point that is obtained from a corneal curvature center that is calculated using a general curvature radius value. A gaze point 166 indicates a gaze point that is obtained from a corneal curvature center that is calculated using a distance 126 obtained in the calibration process. The pupil center 112C indicates the pupil center that is calculated in the calibration process, and the corneal reflection center 113C indicates the corneal reflection center that is calculated in the calibration process. A straight line 173 is a straight line that connects the virtual light source 103V and the corneal reflection center 113C. The corneal curvature center 110 is a position of the corneal curvature center that is calculated from a general curvature radius value. The distance 126 is a distance between the pupil center 112C that is calculated in the calibration process and the corneal curvature center 110. A corneal curvature center 110H indicates a position of a corrected corneal curvature center that is obtained by correcting the corneal curvature center 110 using the distance 126. The corneal curvature center 110H is obtained under the condition that the corneal curvature center 110 is located on the straight line 173 and the distance between the pupil center 112C and the corneal curvature center 110 is the distance 126. Accordingly, a line of sight 177 that is calculated using a general curvature radius value is corrected to a line of sight 178. Further, the gaze point on the display screen 101S of the display device 101 is corrected from the gaze point 165 to the gaze point 166.

Evaluation Method

The evaluation method according to the present embodiment will be described below. In the evaluation method according to the present embodiment, cognitive impairment and brain impairment of the subject are evaluated by using the line-of-sight detection apparatus 100 as described above.

Figure 8:
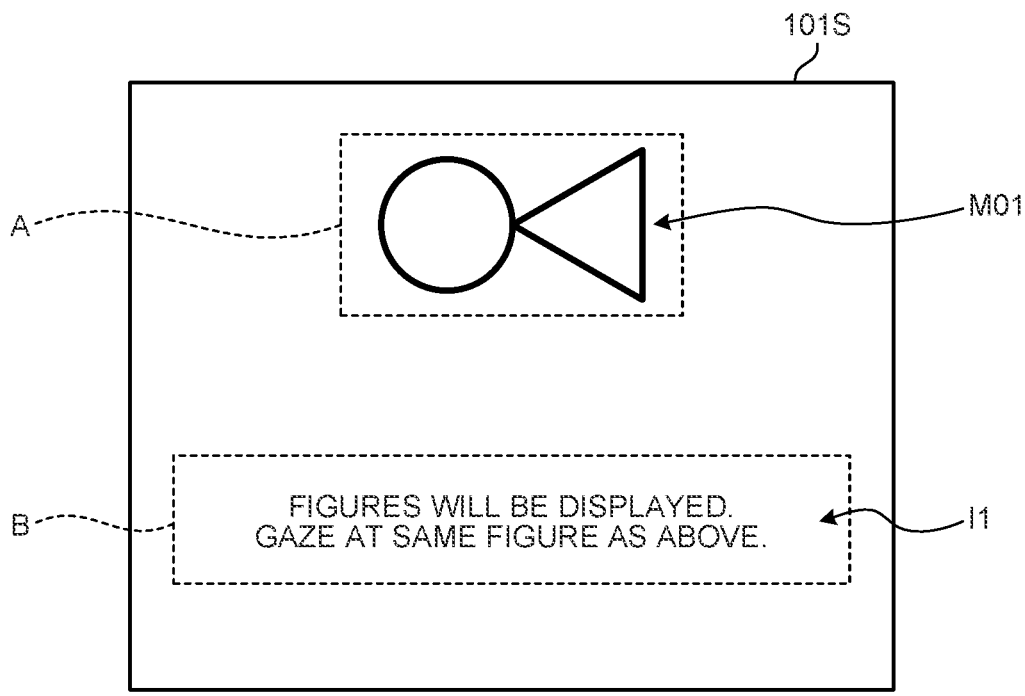
FIG. 8 is a diagram illustrating an example of contents that are displayed on a display screen in instruction display operation.

FIG. 8 is a diagram illustrating an example of contents that are displayed on the display screen 101S in the instruction display operation. As illustrated in FIG. 8, in the instruction display operation, the display control unit 202 displays, on the display screen 101S, a task target object M01 to be gazed at by the subject and instruction information I1 for instructing the subject to solve a task related to the task target object M01. In this case, a task of memorizing a figure of the task target object M01 and selecting the same target object as the memorized task target object M01 is illustrated as an example. The display control unit 202 displays the task target object M01 and the instruction information I1 in a non-overlapping manner on the display screen 101S.

During the instruction display period in which the instruction display operation is performed, the region setting unit 216 sets a task region A in a rectangular range including the task target object M01, for example. Further, the region setting unit 216 sets an instruction region B in a rectangular range including the instruction information I1, for example. The region setting unit 216 sets the task region A and the instruction region B in a non-overlapping manner on the display screen 101S. Meanwhile, the task region A and the instruction region B need not always have rectangular shapes, but may have different shapes, such as circles, ellipses, or polygons.

Figure 9:
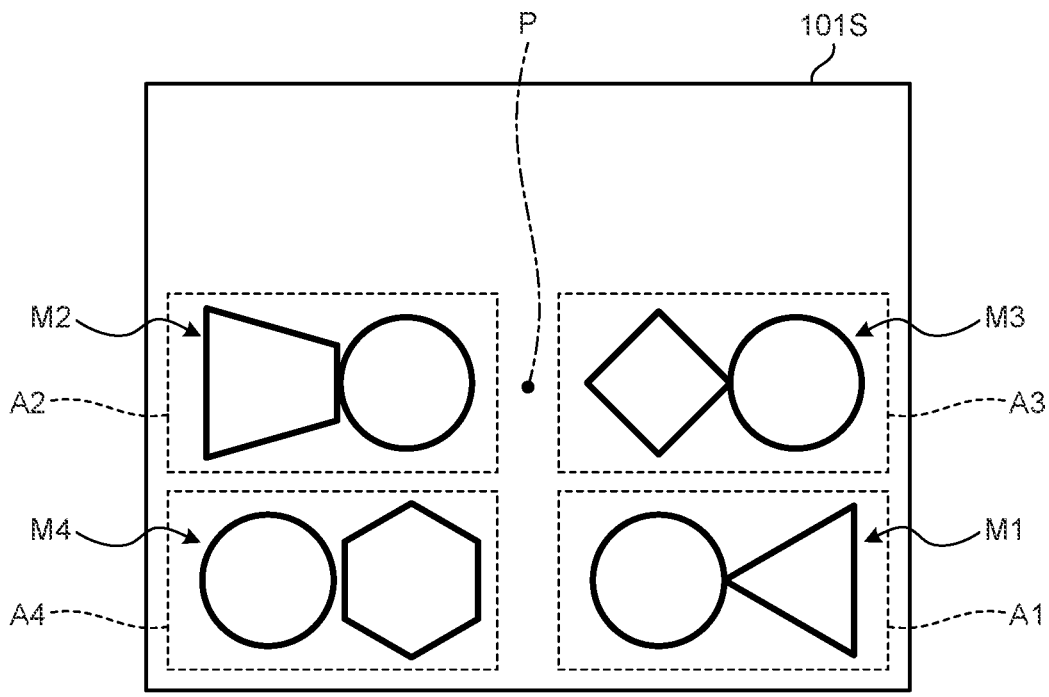
FIG. 9 is a diagram illustrating an example of a case in which a plurality of target objects are displayed on the display screen in target display operation.

FIG. 9 is a diagram illustrating an example of a case in which a plurality of target objects are displayed on the display screen 101S in the target display operation. After performing the instruction display operation for a predetermined period, the display control unit 202 displays, as the target display operation, a specific target object M1 that is a correct answer for the instruction information I1 and a plurality of comparison target objects M2 to M4 that are incorrect answers for the instruction information I1 on the display screen 101S as illustrated in FIG. 9.

The comparison target objects M2 to M4 may have similar shapes to the specific target object M1, or may have dissimilar shapes to the specific target object M1. In the example illustrated in FIG. 9, the comparison target object M2 has a shape formed by combining a trapezoid and a circle, the comparison target object M3 has a shape formed by combining a square and a circle, and the comparison target object M4 has a shape formed by combining a circle and a regular hexagon. The display control unit 202 displays the plurality of target objects including the specific target object M1 and the comparison target objects M2 to M4 on the display screen 101S, and instructs the subject to find the specific target object M1 and gaze at the found specific target object M1.

Meanwhile, FIG. 9 illustrates one example of a gaze point P that is displayed, as a result, on the display screen 101S after measurement for example, but in reality, the gaze point P is not displayed on the display screen 101S. Positional data of the gaze point P is detected with a period of the frame synchronous signal (for example, every 20 msec) that is output from the first camera 102A and the second camera 102B, for example. The first camera 102A and the second camera 102B capture images in a synchronous manner.

During the target display period in which the target display operation is performed, the region setting unit 216 sets a specific region A1 that corresponds to the specific target object M1. Furthermore, the region setting unit 216 sets comparison regions A2 to A4 that respectively correspond to the comparison target objects M2 to M4. Meanwhile, the specific region A1 and the comparison regions A2 to A4 are not displayed on the display screen 101S.

The region setting unit 216 sets the specific region A1 in a rectangular range including the specific target object M1, for example. Similarly, the region setting unit 216 sets the comparison regions A2 to A4 in respective rectangular ranges including the comparison target objects M2 to M4, for example. Meanwhile, the specific region A1 and the comparison regions A2 to A4 need not always have rectangular shapes, but may have different shapes, such as circles, ellipses, or polygons. The display control unit 202 sets the specific region A1 and the comparison regions A2 to A4 in a non-overlapping manner on the display screen 101S.

It is known that symptoms of cognitive impairment and brain impairment affect cognitive ability and memory ability of the subject. If the subject does not have cognitive impairment and brain impairment, the subject views the instruction information I1 that is displayed on the display screen 101S in the instruction display operation, and thereafter attempts to gaze at the task target object M01 indicated by the instruction information I1 and memorize the shape of the task target object M01. Further, if the subject does not have cognitive impairment and brain impairment, the subject is able to view, one by one, the comparison target objects M2 to M4 that are displayed on the display screen 101S in the target display operation, determine, by comparison, that the comparison target objects M2 to M4 are not the same as the specific target object M1 that is memorized in the instruction display operation, and finally detect and gaze at the specific target object M1.

In contrast, if the subject has cognitive impairment and brain impairment, the subject tends to continuously view the instruction information I1 or alternately view the instruction information I1 and the task target object M01 in the instruction display operation, and not to view the task target object M01 in a concentrated manner. Further, if the subject has cognitive impairment and brain impairment, the subject may have difficulty in memorizing the specific target object M1 in the instruction display operation or may immediately forget the specific target object M1 after memorizing it. Therefore, it may be difficult to perform comparison as described above in the target display operation, and it may be difficult to gaze at the specific target object M1.

Furthermore, in a method of displaying the plurality of target objects M1, M2, M3, and M4 on the display screen 101S in the target display operation, in some cases, the gaze point of the subject may be accidentally located at the specific target object M1 that is a correct answer at the start of the target display operation. In this case, it may be determined that the answer is correct regardless of whether or not the subject has cognitive impairment and brain impairment, so that it becomes difficult to evaluate the subject with high accuracy. To cope with this, it is possible to evaluate the subject through the procedure as described below, for example.

First, as the instruction display operation, the task target object M01 and the instruction information I1 are displayed on the display screen 101S. In this case, it is possible to evaluate the subject from the standpoint of whether the subject, after viewing the instruction information I1 displayed on the display screen 101S, is attempting to gaze at the task target object M01 indicated by the instruction information I1 and memorize the shape of the task target object M01. Further, it is possible to evaluate the subject from a different standpoint of whether the subject is continuously viewing the instruction information I1, whether the subject is alternately viewing the instruction information I1 and the task target object M01, or whether the subject is not viewing the task target object M01 in a concentrated manner in the instruction display operation.

Furthermore, as the target display operation, the specific target object M1 and the plurality of comparison target objects M2 to M4 are displayed on the display screen 101S. In this case, it is possible to evaluate the subject from the standpoint of whether the subject gazes at the plurality of comparison target objects M2 to M4 one by one, whether the subject is able to finally reach the specific target object M1 that is a correct answer, how long does it take before the subject reaches the specific target object M1, and whether the subject is able to gaze at the specific target object M1, for example.

For example, in the instruction display operation, if the positional data of the gaze point P of the subject is detected, the determination unit 218 determines whether the gaze point of the subject is present in the task region A and the instruction region B, and outputs determination data.

The arithmetic unit 220 calculates instruction movement course data indicating the course of movement of the gaze point P during the instruction display period, on the basis of the determination data. The arithmetic unit 220 calculates, as the instruction movement course data, the first presence time data, the second presence time data, the instruction arrival time data, and the instruction movement frequency data.

The first presence time data indicates presence time in which the gaze point P is present in the task region A. In the present embodiment, it is possible to estimate that the presence time in which the gaze point P is present in the task region A increases with an increase in the number of times the gaze point is determined as being present in the task region A by the determination unit 218. Therefore, it is possible to adopt, as the first presence time data, the number of times the gaze point is determined as being present in the task region A by the determination unit 218. In other words, the arithmetic unit 220 is able to adopt a count value CNTA of the counter as the first presence time data.

The second presence time data indicates presence time in which the gaze point P is present in the instruction region B. In the present embodiment, it is possible to estimate that the presence time in which the gaze point P is present in the instruction region B increases with an increase in the number of times the gaze point is determined as being present in the instruction region B by the determination unit 218. Therefore, it is possible to adopt, as the second presence time data, the number of times the gaze point is determined as being present in the instruction region B by the determination unit 218. In other words, the arithmetic unit 220 is able to adopt a count value CNTB of the counter as the first presence time data.

The instruction arrival time data indicates a time period from the start time of the instruction display period to an arrival time at which the gaze point first arrives at the task region A. Therefore, by measuring an elapsed time since the start of the instruction display period by the timer T1 and detecting a measurement value of the timer T1 by assuming that a flag value is set to 1 at the time the gaze point first arrives at the task region A, the arithmetic unit 220 is able to adopt a detection result of the timer T1 as the instruction arrival time data.

The instruction movement frequency data indicates the number of times of movement of the gaze point P between the task region A and the instruction region B. Therefore, the arithmetic unit 220 is able to count the number of times of movement of the gaze point P between the regions, i.e., between the task region A and the instruction region B, and adopt a count result as the instruction movement frequency data.

With respect to the instruction display operation, the evaluation unit 224 obtains evaluation data on the basis of the first presence time data, the second presence time data, the instruction arrival time data, and the instruction movement frequency data.

Here, a data value of the first presence time data is denoted by D11, a data value of the second presence time data is denoted by D12, a data value of the instruction arrival time data is denoted by D13, and a data value of the instruction movement frequency data is denoted by D14. In this regard, however, it is assumed that the data value D11 of the first presence time data is the number of seconds in which the gaze point P is present in the task region A, and is set to a if the number of seconds is equal to or larger than a predetermined upper limit a. Further, the data value D12 of the second presence time data is set to a value that is obtained by subtracting the number of seconds in which the gaze point P is present in the instruction region B from the value a as described above. Furthermore, the data value D13 of the instruction arrival time data is set to a reciprocal of the arrival time (for example, 1/(arrival time)/10) (10 is a coefficient used to set an arrival time evaluation value to 1 or smaller based on the assumption that a minimum value of the arrival time is 0.1 second). Moreover, the data value D14 of the instruction movement frequency data is a value that is obtained by subtracting a counter value from 1. Meanwhile, when the data value D14 is to be calculated, it may be possible to set an upper limit of the counter value that is to be subtracted from 1.

In this case, an evaluation value ANS may be represented as follows, for example.

$$ANS1=D11\times K11+D12\times K12+D13\times K13+D14\times K14$$

Meanwhile, K11 to K14 are constants for weighting. The constants K11 to K14 may be set appropriately.

A value of the evaluation value ANS1 represented by Expression above increases with an increase in the data value D11 of the first presence time data, with an increase in the data value D12 of the second presence time data, with an increase in the data value D13 of the instruction arrival time data, and with an increase in the data value D14 of the instruction movement frequency data. In other words, the evaluation value AN1 increases with an increase in the presence time of the gaze point P in the task region A, with a decrease in the presence time of the gaze point P in the instruction region B, with a decrease in the arrival time at which the gaze point P arrives at the task region A since the start time of the instruction display period, and with a decrease in the number of times of movement of the gaze point P between the task region A and the instruction region B.

In contrast, the value of the evaluation value AN1 decreases with a decrease in the data value D11 of the first presence time data, with a decrease in the data value D12 of the second presence time data, with a decrease in the data value D13 of the instruction arrival time data, and with a decrease in the data value D14 of the instruction movement frequency data. In other words, the evaluation value AN1 decreases with a decrease in the presence time of the gaze point P in the task region A, with an increase in the presence time of the gaze point P in the instruction region B, with an increase in the arrival time at which the gaze point P arrive at the task region A since the start time of the instruction display period, and with an increase in the number of times of movement of the gaze point P between the task region A and the instruction region B.

Therefore, the evaluation unit 224 is able to obtain the evaluation data by determining whether the evaluation value AN1 is equal to or larger than a predetermined value. For example, if the evaluation value AN1 is equal to or larger than the predetermined value, it is possible to evaluate that the subject is less likely to have cognitive impairment and brain impairment. Further, if the evaluation value AN1 is smaller than the predetermined value, it is possible to evaluate that the subject is highly likely to have cognitive impairment and brain impairment.

Furthermore, for example, if the positional data of the gaze point P of the subject is detected in the target display operation, the determination unit 218 determines whether the gaze point of the subject is present in the specific region A1 and the plurality of comparison regions A2 to A4, and outputs determination data.

The arithmetic unit 220 calculates the target movement course data indicating the course of movement of the gaze point P during the target display period, on the basis of the determination data. The arithmetic unit 220 calculates, as the target movement course data, the target presence time data, the target movement frequency data, the final region data, and the target arrival time data.

The target presence time data indicates the presence time in which the gaze point P is present in the specific region A1. In the present embodiment, it is possible to estimate that the presence time in which the gaze point P is present in the specific region A1 increases with an increase in the number of times the gaze point is determined as being present in the specific region A1 by the determination unit 218. Therefore, it is possible to adopt, as the target presence time data, the number of times the gaze point is determined as being present in the specific region A1 by the determination unit 218. In other words, the arithmetic unit 220 is able to adopt a count value CNTA1 of the counter as the target presence time data.

The target movement frequency data indicates the number of times of movement of the position of the gaze point P among the plurality of comparison regions A2 to A4 before the gaze point P first arrives at the specific region A1. Therefore, the arithmetic unit 220 is able to count the number of times of movement of the gaze point P among the specific region A1 and the comparison regions A2 to A4, and adopt, as the target movement frequency data, a result of counting that is performed before the gaze point P arrives at the specific region A1.

Further, the final region data indicates a region in which the gaze point P is finally located among the specific region A1 and the comparison regions A2 to A4, that is, a region that is finally gazed at, as an answer, by the subject. The arithmetic unit 220 updates a region in which the gaze point P is present every time the gaze point P is detected, and is accordingly able to adopt a detection result at the end of the target display period as the final region data.

Furthermore, the target arrival time data indicates a time period from the start time of the target display period to an arrival time at which the gaze point first arrives at the specific region A1. Therefore, by measuring an elapsed time since the start of the target display period by the timer T1 and detecting a measurement value of the timer T1 by assuming that the flag value is set to 1 at the time the gaze point first arrives at the specific region A1, the arithmetic unit 220 is able to adopt a detection result of the timer T1 as the target arrival time data.

With respect to the target display operation, the evaluation unit 224 obtains evaluation data on the basis of the target presence time data, the target movement frequency data, the final region data, and the target arrival time data.

Here, a data value of the final region data is denoted by D21, a data value of the target presence time data is denoted by D22, a data value of the target arrival time data is denoted by D23, and a data value of the target movement frequency data is denoted by D24. However, the data value D21 of the final region data is set to 1 if the final gaze point P of the subject is present in the specific region A1 (that is, if the answer is correct), and set to 0 if the gaze point P of the subject is not present in the specific region A1 (that is, if the answer is incorrect). Further, it is assumed that the data value D22 of the target presence time data is the number of seconds in which the gaze point P is present in the specific region A1. Meanwhile, it may be possible to set, for the data value D22, an upper limit value that is a smaller number of seconds than the display period. Furthermore, the data value D23 of the target arrival time data is set to a reciprocal of the arrival time (for example, 1/(arrival time)/10) (10 is a coefficient used to set an arrival time evaluation value to 1 or smaller based on the assumption that a minimum value of the arrival time is 0.1 second). Moreover, the counter value is used as it is as the data value D24 of the target movement frequency data. Meanwhile, it may be possible to appropriately set an upper limit of the data value D24.

In this case, an evaluation value ANS may be represented as follows, for example.

$$ANS2=D21\times K21+D22\times K22+D23\times K23+D24\times K24$$

Meanwhile, K21 to K24 are constants for weighting. The constants K21 to K24 may be set appropriately.

A value of the evaluation value ANS2 represented by Expression above increases when the data value D21 of the final region data is set to 1, when the data value D22 of the target presence time data increases, when the data value D23 of the target arrival time data increases, and when a value of the data value D24 of the target movement frequency data increases. In other words, the evaluation value ANS2 increases when the final gaze point P is present in the specific region A1, when the presence time of the gaze point P in the specific region A1 increases, when the arrival time at which the gaze point P arrives at the specific region A1 since the start time of the target display period decreases, and when the number of times of movement of the gaze point P among the regions increases.

In contrast, the value of the evaluation value ANS2 decreases when the data value D21 of the final region data is set to 0, when the data value D22 of the target presence time data decreases, when the data value D23 of the target arrival time data decreases, and when the data value D24 of the target movement frequency data decreases. In other words, the evaluation value ANS2 decreases when the final gaze point P is not present in the specific region A1, when the presence time of the gaze point P in the specific region A1 decreases, when the arrival time at which the gaze point P arrives at the specific region A1 since the start time of the target display period increases, and when the number of times of movement of the gaze point P among the regions decreases.

Therefore, the evaluation unit 224 is able to obtain the evaluation data by determining whether the evaluation value ANS2 is equal to or larger than a predetermined value. For example, if the evaluation value ANS2 is equal to or larger than the predetermined value, it is possible to evaluate that the subject is less likely to have cognitive impairment and brain impairment. Further, if the evaluation value ANS2 is smaller than the predetermined value, it is possible to evaluate that the subject is highly likely to have cognitive impairment and brain impairment.

Furthermore, the evaluation unit 224 is able to store the value of the evaluation value ANS2 in the storage unit 222. For example, it may be possible to cumulatively store the evaluation values ANS2 for the same subject, and perform evaluation by comparison with past evaluation values. For example, if the evaluation value ANS2 has a higher value than a past evaluation value, it is possible to evaluate that a cognitive function and a brain function have improved relative to those at the previous evaluation. Moreover, if a cumulative value of the evaluation value ANS2 is gradually increased for example, it is possible to evaluate that the cognitive function and the brain function have gradually improved.

Furthermore, the evaluation unit 224 may perform evaluation by using the target presence time data, the target movement frequency data, the final region data, and the target arrival time data independently or in combination. For example, if the gaze point P accidentally arrives at the specific region A1 while a number of target objects are viewed, the data value D24 of the target movement frequency data decreases. In this case, it is possible to perform evaluation by additionally using the data value D22 of the target presence time data as described above. For example, even when the number of times of movement is small, if the presence time is long, it is possible to evaluate that the specific region A1 as the correct answer is gazed at. Moreover, if the number of times of movement is small and the presence time is short, it is possible to evaluate that the gaze point P has accidentally passed through the specific region A1.

Furthermore, when the number of times of movement is small, and if the final region is the specific region A1, it is possible to evaluate that the gaze point arrives at the specific region A1 that is the correct answer through a small number of times of movement, for example. In contrast, when the number of times of movement as described above is small, and if the final region is not the specific region A1, it is possible to evaluate that the gaze point P has accidentally passed through the specific region A1, for example.

Meanwhile, the evaluation unit 224 may perform evaluation by a combination of the evaluation value ANS1 obtained in the instruction display operation and the evaluation value ANS2 obtained in the target display operation.

In the present embodiment, when the evaluation unit 224 outputs the evaluation data, the output control unit 226 is able to cause the output device 50 to output character data indicating that "it seems that the subject is less likely to have cognitive impairment and brain impairment" or character data indicating that "it seems that the subject is highly likely to have cognitive impairment and brain impairment" in accordance with the evaluation data, for example. Further, if the evaluation value ANS has increased relative to a past evaluation value ANS of the same subject, the output control unit 226 is able to cause the output device 50 to output character data indicating that "the cognitive function and the brain function have improved" or the like.

Figure 10:
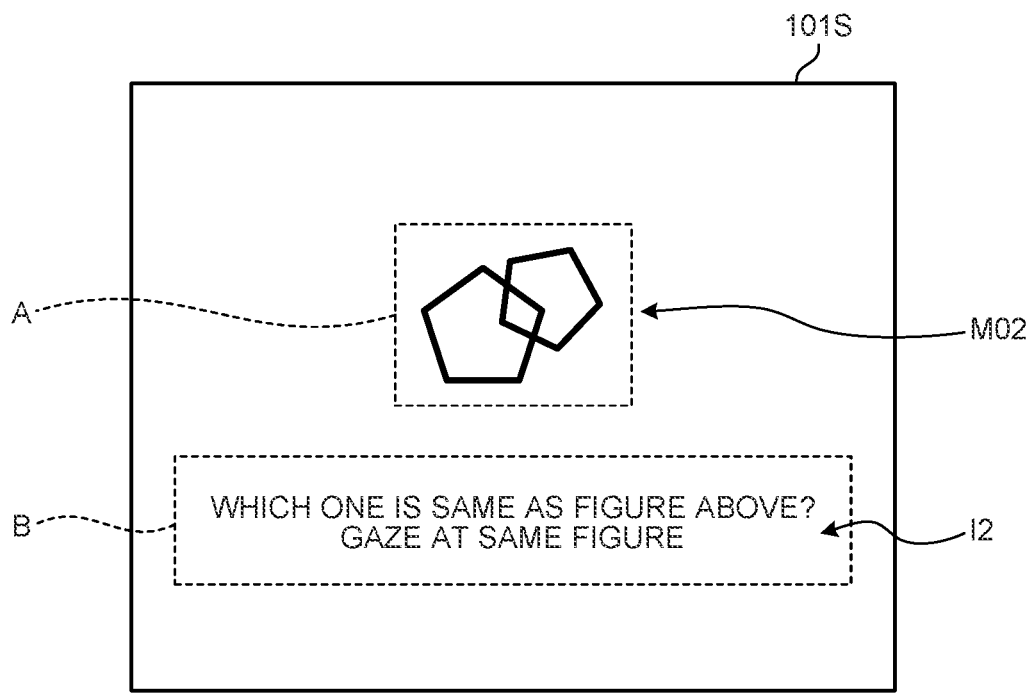
FIG. 10 is a diagram illustrating another example of contents that are displayed on the display screen in the instruction display operation.

FIG. 10 is a diagram illustrating another example of contents that are displayed on the display screen 101S in the instruction display operation. As illustrated in FIG. 10, in the instruction display operation, the display control unit 202 displays a task target object M02 on the display screen 101S, and simultaneously displays instruction information I2 for instructing the subject to gaze at the same figure as the task target object M02 on the display screen 101S. The region setting unit 216 sets the task region A in a rectangular range including the task target object M02, for example. Further, the region setting unit 216 sets the instruction region B in a rectangular region including the instruction information I2, for example. The region setting unit 216 sets the task region A and the instruction region B in a non-overlapping manner on the display screen 101S.

Figure 11:
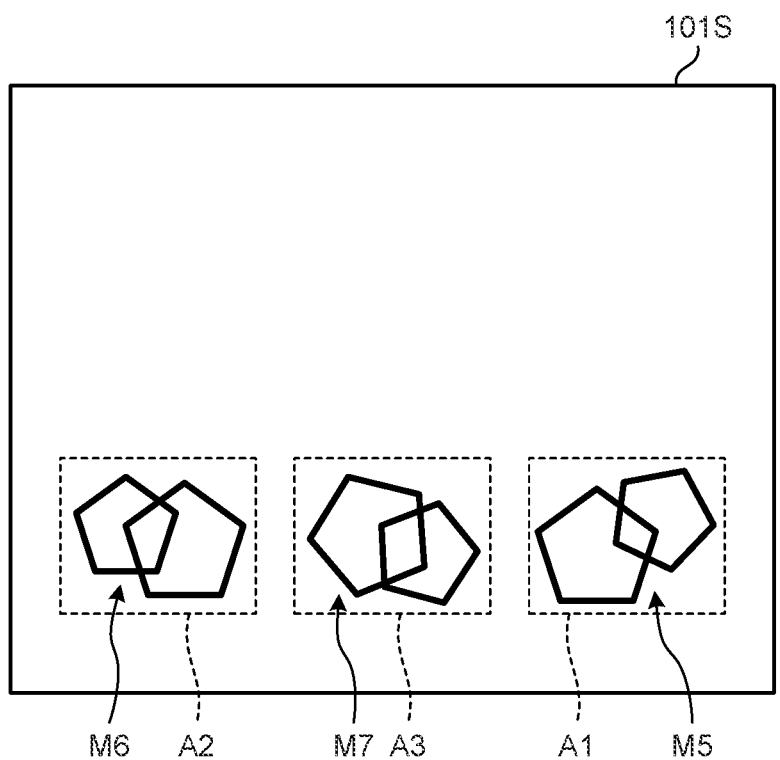
FIG. 11 is a diagram illustrating another example of a case in which a plurality of target objects are displayed on the display screen in the target display operation.

FIG. 11 is a diagram illustrating another example of a case in which a plurality of target objects are displayed on the display screen 101S in the target display operation. After the instruction display operation, the display control unit 202 displays, in the target display operation, a specific target object M5 that is a correct answer for the instruction information I2 and comparison target objects M6 and M7 that are incorrect answers for the instruction information I2 as illustrated in FIG. 11. In this case, the display control unit 202 displays figures, all of which are formed of the same shapes (for example, pentagons), like the specific target object M5 and the comparison target objects M6 and M7, for example. Further, the region setting unit 216 is able to set the specific region A1 corresponding to the specific target object M5, and set the comparison regions A2 and A3 corresponding to the comparison target objects M6 and M7. The region setting unit 216 sets the specific region A1 and the comparison regions A2 and A3 in a non-overlapping manner on the display screen 101S. In this manner, in the target display operation, by displaying the specific target object M5 and the comparison target objects M6 and M7 that are similar figures, it is possible to also evaluate figure recognition ability of the subject.

Figure 12:
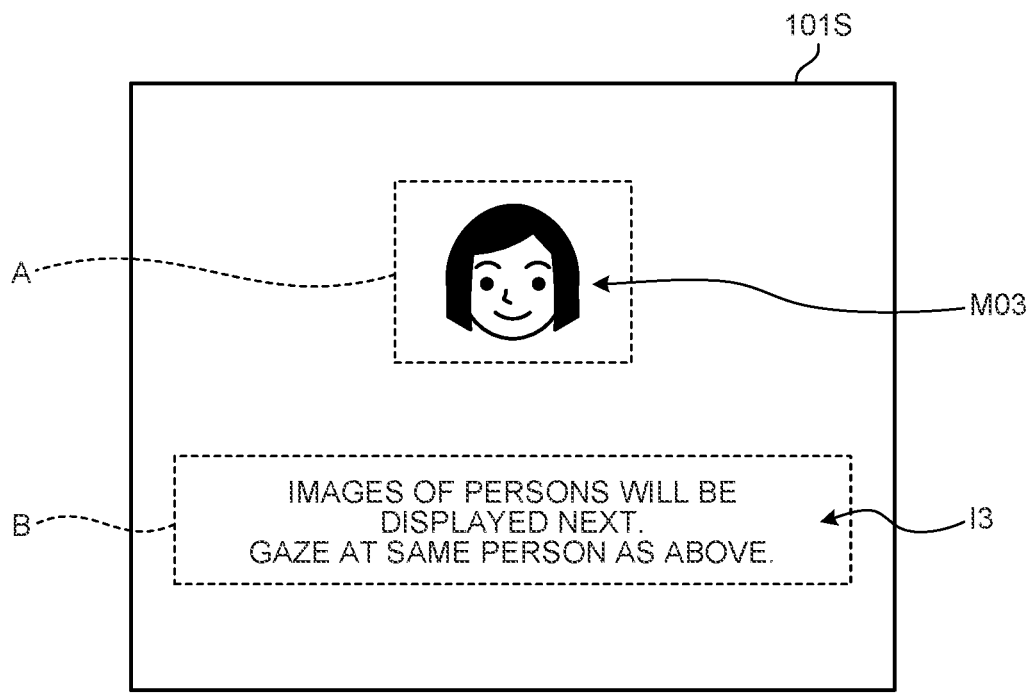
FIG. 12 is a diagram illustrating still another example of contents that are displayed on the display screen in the instruction display operation.

FIG. 12 is a diagram illustrating still another example of contents that are displayed on the display screen 101S in the instruction display operation. As illustrated in FIG. 12, in the instruction display operation, the display control unit 202 may display, as a task target object M03, a face of a person on the display screen 101S, and simultaneously display instruction information 13 for instructing the subject to gaze at the same person as the task target object M03 on the display screen 101S. In this case, the region setting unit 216 sets the task region A in a rectangular range including the task target object M03, for example. Further, the region setting unit 216 sets the instruction region B in a rectangular range including the instruction information 13, for example. The region setting unit 216 sets the task region A and the instruction region B in a non-overlapping manner on the display screen 101S.

Figure 13:
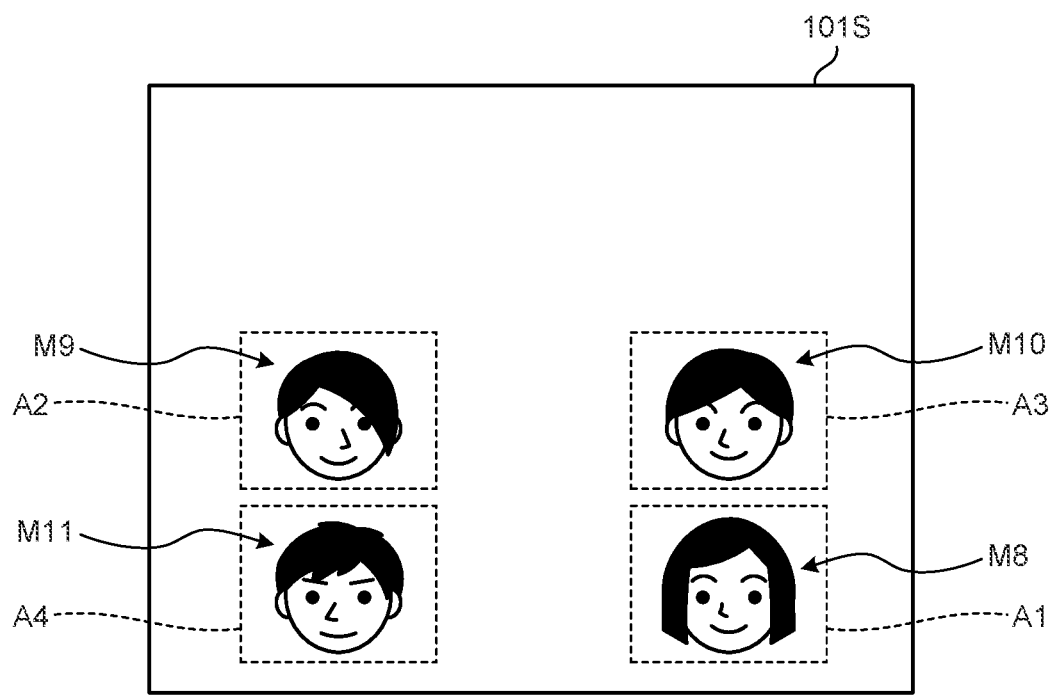
FIG. 13 is a diagram illustrating still another example of a case in which a plurality of target objects are displayed on the display screen in the target display operation.

FIG. 13 is a diagram illustrating still another example of a case in which a plurality of target objects are displayed on the display screen 101S in the target display operation. After the instruction display operation, the display control unit 202 displays, in the target display operation, a specific target object M8 that represents a face of the same person as a task target object that is a correct answer for the instruction information 13, and comparison target objects M9 to M11 that represent faces of persons different from the specific target object M8 and that are incorrect answers for the instruction information 13 on the display screen 101S as illustrated in FIG. 13. Further, the region setting unit 216 sets the specific region A1 corresponding to the specific target object M8, and sets the comparison regions A2 to A4 corresponding to the comparison target objects M9 to M11. The region setting unit 216 sets the specific region A1 and the comparison regions A2 to A4 in a non-overlapping manner on the display screen 101S. In this manner, by displaying faces of persons in the instruction display operation and the target display operation, it is possible to evaluate face recognition ability of the subject.

Figure 14:
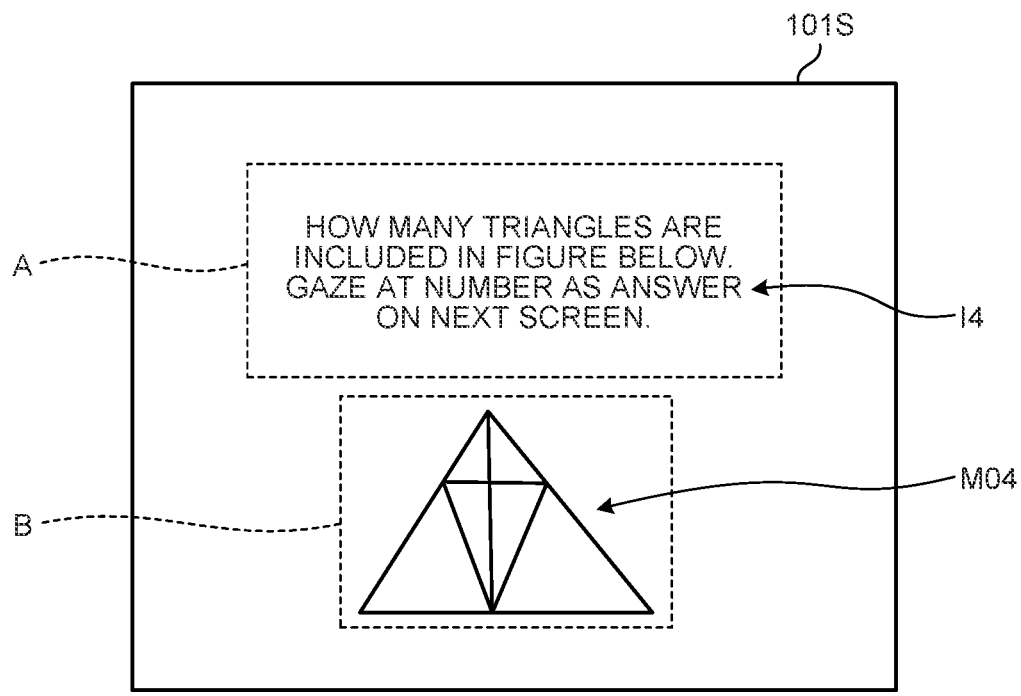
FIG. 14 is a diagram illustrating still another example of contents that are displayed on the display screen in the instruction display operation.

FIG. 14 is a diagram illustrating still another example of contents that are displayed on the display screen 101S in the instruction display operation. In the instruction display operation, the display control unit 202 may display, as a task target object M04, a figure including a plurality of triangles on the display screen 101S, and display, as instruction information 14, an instruction for instructing the subject to obtain the number of triangles included in the task target object M04 and gaze at a correct numeral on the display screen 101S. In this manner, the task given to the subject is not limited to memorizing of a task target object. Further, the region setting unit 216 sets the task region A in a rectangular range including the task target object M04, for example. Furthermore, the region setting unit 216 sets the instruction region B in a rectangular range including the instruction information 14, for example. The region setting unit 216 sets the task region A and the instruction region B in a non-overlapping manner on the display screen 101S.

Figure 15:
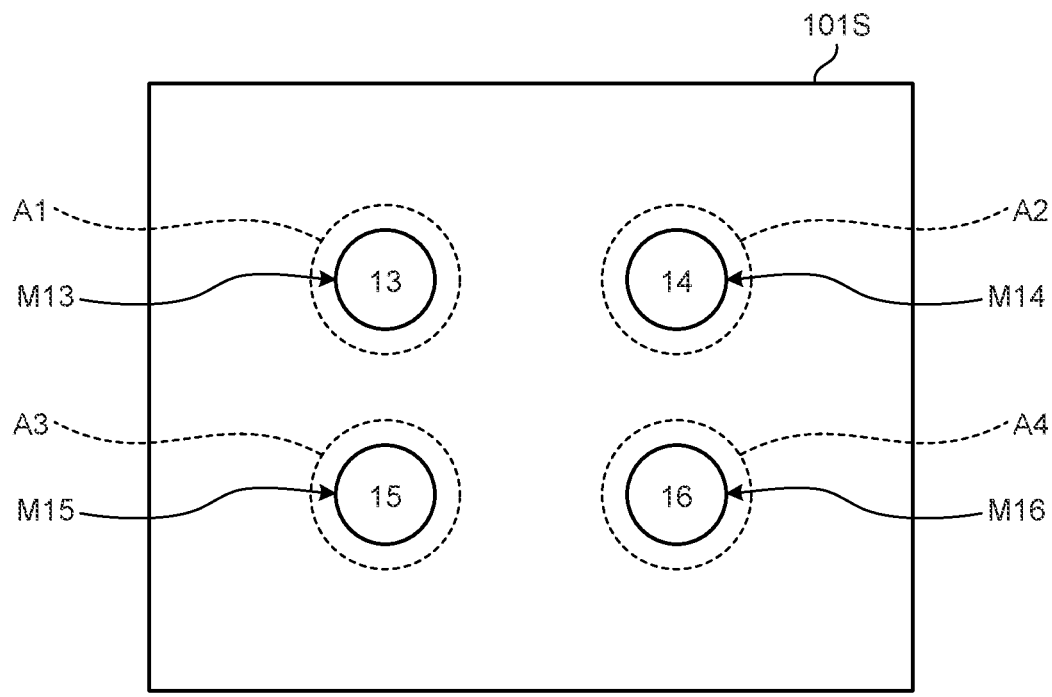
FIG. 15 is a diagram illustrating still another example of the case in which a plurality of target objects are displayed on the display screen in the target display operation.

FIG. 15 is a diagram illustrating still another example of a case in which a plurality of target objects are displayed on the display screen 101S in the target display operation. After the instruction display operation, the display control unit 202 displays, in the target display operation, a plurality of target objects M13 to M16 indicating numbers of "13" to "16" on the display screen 101S as illustrated in FIG. 15. The display control unit 202 displays, as the plurality of target objects M13 to M16, the specific target object M13 that is a correct answer for the instruction information 14 and displays the comparison target objects M14 to M16 that are different from the specific target object M13 and that are incorrect answers for the instruction information 14 on the display screen 101S. Further, the region setting unit 216 sets the specific region A1 corresponding to the specific target object M13, and sets the comparison regions A2 to A4 corresponding to the comparison target objects M14 to M16. The region setting unit 216 sets the specific region A1 and the comparison regions A2 to A4 in a non-overlapping manner on the display screen 101S.

In this setting, when the data value D21 is obtained in the evaluation, and if the final gaze point P of the subject is not present in the specific region A1, it is possible to assign a certain data value in order from the closest value to the correct answer, instead of setting the data value D21 to 0. For example, it may be possible to obtain, as the data value D21, 0.6 when the final gaze point P of the subject is present in the comparison region A2, 0.2 when the final gaze point P of the subject is present in the comparison region A3, and 0 when the final gaze point P of the subject is present in the comparison region A4. Thus, in this manner, it is possible to set a wide variety of tasks given to the subject, and it is possible to perform evaluation more precisely.

Figure 16:
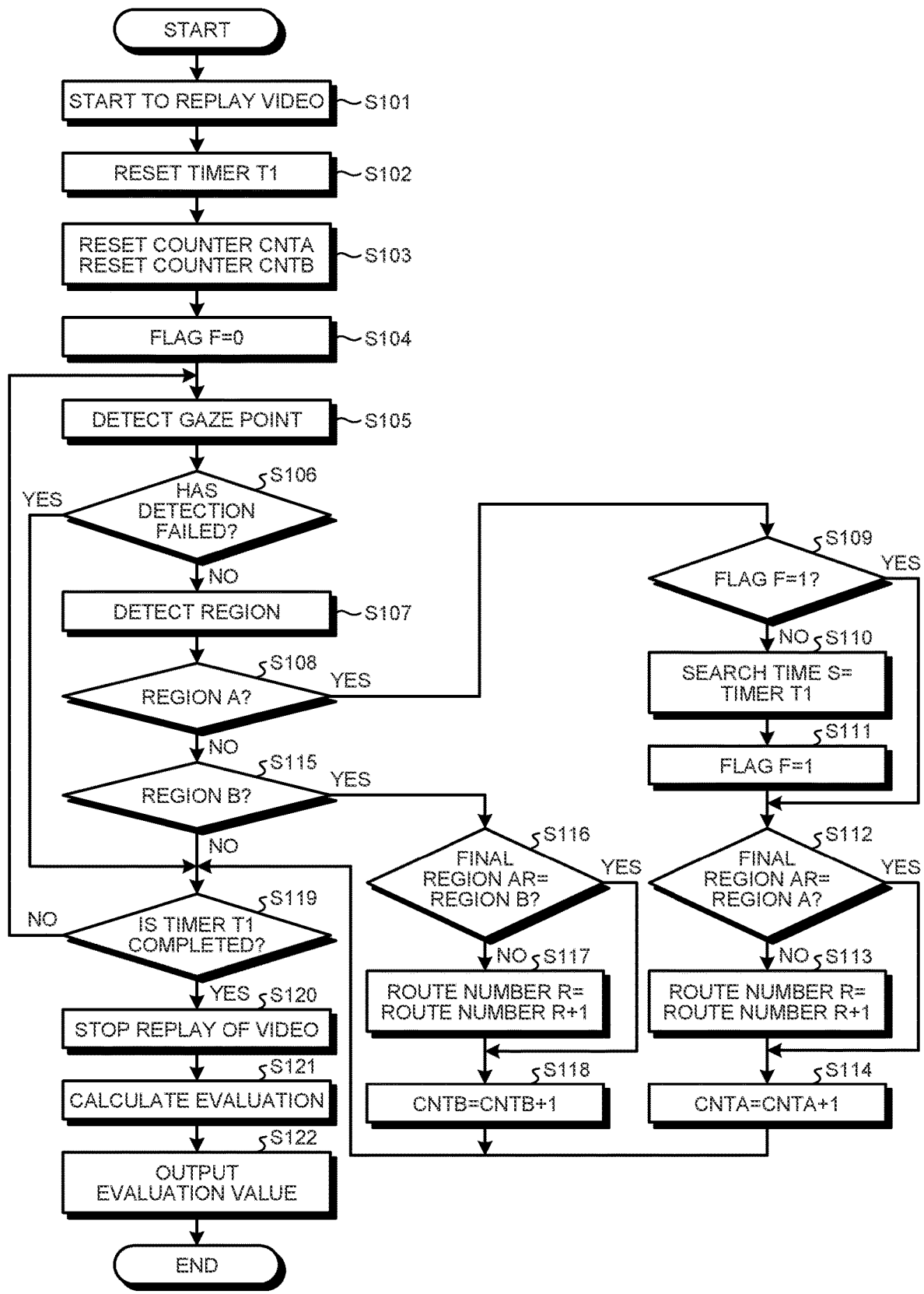
FIG. 16 is a flowchart illustrating an example of an evaluation method in the instruction display operation.

Next, an example of the evaluation method according to the present embodiment will be described. First, an example of the evaluation method in the instruction display operation will be described. FIG. 16 is a flowchart illustrating an example of the evaluation method in the instruction display operation. As illustrated in FIG. 16, in the instruction display operation, the display control unit 202 starts to replay a video (Step S101), and thereafter resets the timer T1 (Step S102), resets the count values CNTA and CNTB of the counter (Step S103), and sets the flag value F to 0 (Step S104).

The gaze point detection unit 214 detects the positional data of the gaze point of the subject on the display screen 101S of the display device 101 with a defined sampling period (for example, 20 msec) while showing the video displayed on the display device 101 to the subject (Step S105). If the positional data is detected (No at Step S106), the determination unit 218 determines a region in which the gaze point P is present on the basis of the positional data (Step S107). Further, if the positional data is not detected (Yes at Step S106), processes from Step S119 to be described later are performed.

If it is determined that the gaze point P is present in the task region A (Yes at Step S108), the arithmetic unit 220 determines whether the flag value F is set to 1, that is, whether the gaze point P arrived at the task region A for the first time (1: has already arrived, 0: has not arrived yet) (Step S109). If the flag value F is set to 1 (Yes at Step S109), the arithmetic unit 220 skips Step S110 and Step S111 to be described below, and performs a process at Step S112 to be described later.

Further, if the flag value F is not set to 1, that is, if the gaze point P arrived at the task region A for the first time (No at Step S109), the arithmetic unit 220 extracts a measurement result of the timer T1 as the instruction arrival time data (Step S110). Thereafter, the arithmetic unit 220 changes the flag value to 1 (Step S111).

Subsequently, the arithmetic unit 220 determines whether a region in which the gaze point P is present at the last detection, that is, the final region, is the task region A (Step S112). If it is determined that the final region is the task region A (Yes at Step S112), the arithmetic unit 220 skips Step S113 to be described below, and performs a process at Step S114 to be described later. Furthermore, if it is determined that the final region is not the task region A (No at Step S112), the arithmetic unit 220 increments the cumulative number, which indicates the number of times of movement of the gaze point P among the regions, by 1 (Step S113), and increments the count value CNTA, which indicates the first presence time data in the task region A, by 1 (Step S114). Thereafter, the arithmetic unit 220 performs the processes from Step S119 to be described later.

Moreover, if it is determined that the gaze point P is not present in the task region A (No at Step S108), the arithmetic unit 220 determines whether the gaze point P is present in the instruction region B (Step S115). If it is determined that the gaze point P is present in the instruction region B (Yes at Step S115), the arithmetic unit 220 determines whether the region in which the gaze point P is present at the last detection, that is, the final region, is the instruction region B (Step S116). If it is determined that the final region is the instruction region B (Yes at Step S116), the arithmetic unit 220 skips Step S117 to be described below, and performs a process at Step S118 to be described later. Furthermore, if it is determined that the final region is not the instruction region B (No at Step S116), the arithmetic unit 220 increments the cumulative number, which indicates the number of times of movement of the gaze point P among the regions, by 1 (Step S117), and increments the count value CNTB, which indicates the second presence time data in the instruction region B, by 1 (Step S118). After Step S118, and if it is determined, at Step S115, that the gaze point P is not present in the instruction region B (No at Step S115), the arithmetic unit 220 performs the processes from Step S119 to be described later.

Thereafter, the arithmetic unit 220 determines whether a time at which replay of the video is completed has come, on the basis of a detection result of the detection timer T1 (Step S119). If the arithmetic unit 220 determines that the time at which replay of the video is completed has not come (No at Step S119), the arithmetic unit 220 repeats the processes from Step S105 as described above.

If the arithmetic unit 220 determines that the time at which replay of the video is completed has come (Yes at Step S119), the display control unit 202 stops replay of the video related to the instruction display operation (Step S120). After replay of the video is stopped, the evaluation unit 224 calculates the evaluation value ANS1 on the basis of the first presence time data, the second presence time data, the instruction movement frequency data, and the instruction arrival time data that are obtained from processing results as described above (Step S121), and obtains evaluation data on the basis of the evaluation value ANS1. Thereafter, the output control unit 226 outputs the evaluation data obtained by the evaluation unit 224 (Step S122).

Figure 17:
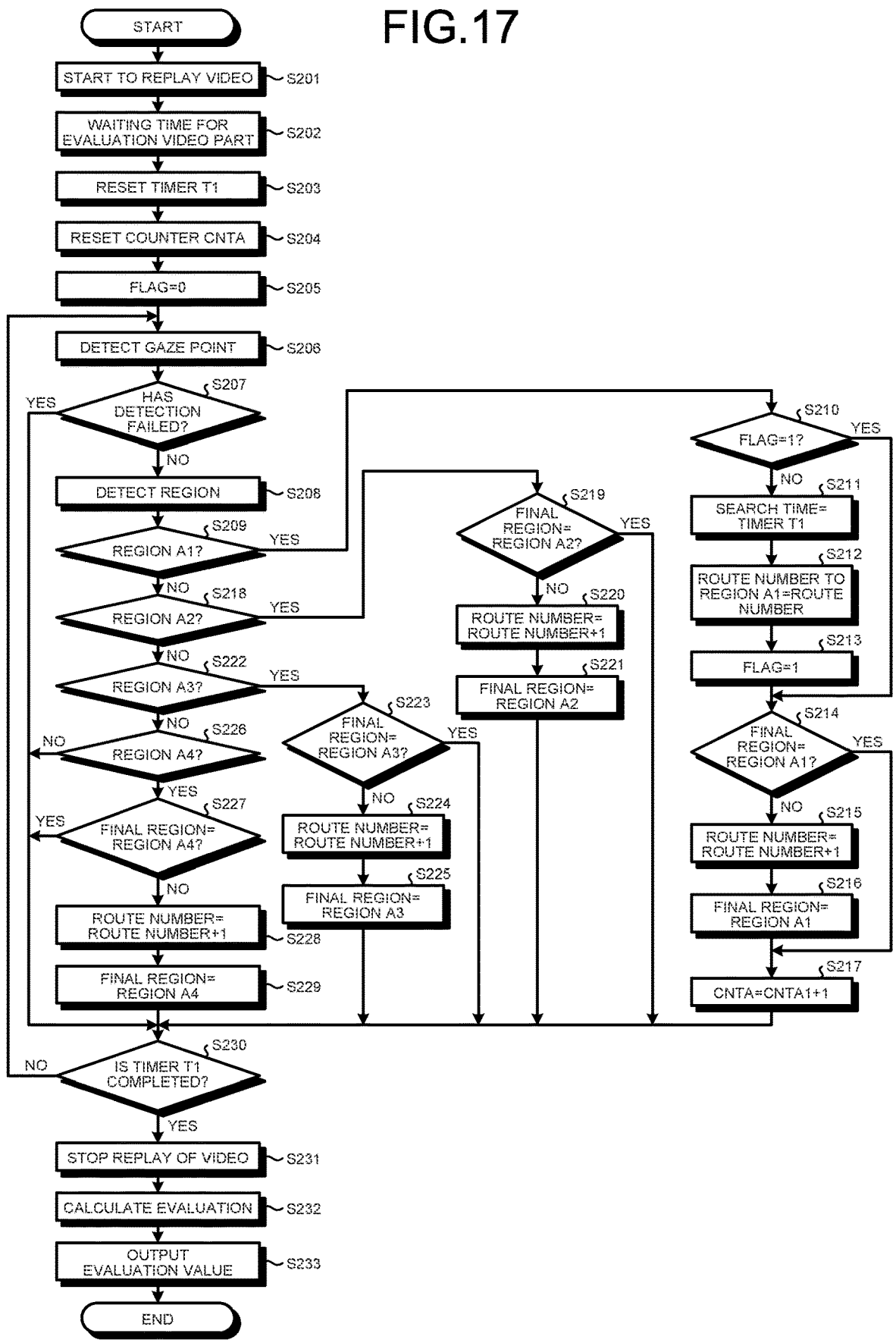
FIG. 17 is a flowchart illustrating an example of an evaluation method in the target display operation.

Next, an example of the evaluation method in the target display operation will be described. FIG. 17 is a flowchart illustrating an example of the evaluation method in the target display operation. As illustrated in FIG. 17, in the target display operation, the display control unit 202 starts to replay the video (Step S201). After a lapse of a waiting time for an evaluation video part (Step S202), the timer T1 is reset (Step S203), the count value CNTA of the counter is reset (Step S204), and the flag value is set to 0 (Step S205).

The gaze point detection unit 214 detects the positional data of the gaze point of the subject on the display screen 101S of the display device 101 with a defined sampling period (for example, 20 msec) while the subject keeps viewing the video displayed on the display device 101 (Step S206). If the positional data is detected (No at Step S207), the determination unit 218 determines a region in which the gaze point P is present on the basis of the positional data (Step S208).

If it is determined that the gaze point P is present in the task region A (Yes at Step S209), the arithmetic unit 220 determines whether the flag value is set to 1, that is, whether the gaze point P arrived at the task region A for the first time (1: has already arrived, 0: has not arrived yet) (Step S210). If the flag value F is set to 1 (Yes at Step S210), the arithmetic unit 220 skips Step S211 to Step S213 to be described below, and performs a process at Step S214 to be described later.

Further, if the flag value is not set to 1, that is, if the gaze point P arrived at the task region A for the first time (No at Step S210), the arithmetic unit 220 extracts a measurement result of the timer T1 as the target arrival time data (Step S211). Furthermore, the arithmetic unit 220 stores movement frequency data, which indicates the number of times of movement of the gaze point P among the regions before the gaze point P arrives at the specific region A1, in the storage unit 222 (Step S212). Thereafter, the arithmetic unit 220 changes the flag value to 1 (Step S213).

Subsequently, the arithmetic unit 220 determines whether a region in which the gaze point P is present at the last detection, that is, the final region, is the specific region A1 (Step S214). If it is determined that the final region is the specific region A1 (Yes at Step S214), the arithmetic unit 220 skips Step S215 and Step S216 to be described below, and performs a process at Step S217 to be described later. Furthermore, if it is determined that the final region is not the specific region A1 (No at Step S214), the arithmetic unit 220 increments the cumulative number, which indicates the number of times of movement of the gaze point P among the regions, by 1 (Step S215), and changes the final region to the specific region A1 (Step S216). Moreover, the arithmetic unit 220 increments the count value CNTA1, which indicates the target presence time data in the specific region A1, by 1 (Step S217). Thereafter, the arithmetic unit 220 performs processes from Step S230 to be described later.

Furthermore, if it is determined that the gaze point P is not present in the specific region A1 (No at Step S209), the arithmetic unit 220 determines whether the gaze point P is present in the comparison region A2 (Step S218). If it is determined that the gaze point P is present in the comparison region A2 (Yes at Step S218), the arithmetic unit 220 determines whether the region in which the gaze point P is present at the last detection, that is, the final region, is the comparison region A2 (Step S219). If it is determined that the final region is the comparison region A2 (Yes at Step S219), the arithmetic unit 220 skips Step S220 and Step S221 to be described below, and performs the processes from Step S230 to be described later. Moreover, if it is determined that the final region is not the comparison region A2 (No at Step S219), the arithmetic unit 220 increments the cumulative number, which indicates the number of times of movement of the gaze point P among the regions, by 1 (Step S215), and changes the final region to the comparison region A2 (Step S220). Thereafter, the arithmetic unit 220 performs the processes from Step S230 to be described later.

Furthermore, if it is determined that the gaze point P is not present in the comparison region A2 (No at Step S218), the arithmetic unit 220 determines whether the gaze point P is present in the comparison region A3 (Step S222). If it is determined that the gaze point P is present in the comparison region A3 (Yes at Step S222), the arithmetic unit 220 determines whether the region in which the gaze point P is present at the last detection, that is, the final region, is the comparison region A3 (Step S223). If it is determined that the final region is the comparison region A3 (Yes at Step S223), the arithmetic unit 220 skips Step S224 and Step S225 to be described below, and performs the process at Step S230 to be described later. Moreover, if it is determined that the final region is not the comparison region A3 (No at Step S223), the arithmetic unit 220 increments the cumulative number, which indicates the number of times of movement of the gaze point P among the regions, by 1 (Step S224), and changes the final region to the comparison region A3 (Step S225). Thereafter, the arithmetic unit 220 performs the processes from Step S230 to be described later.

Furthermore, if it is determined that the gaze point P is not present in the comparison region A3 (No at Step S222), the arithmetic unit 220 determines whether the gaze point P is present in the comparison region A4 (Step S226). If it is determined that the gaze point P is present in the comparison region A4 (Yes at Step S226), the arithmetic unit 220 determines whether the region in which the gaze point P is present at the last detection, that is, the final region, is the comparison region A4 (Step S227). If it is determined that the final region is the comparison region A4 (Yes at Step S227), the arithmetic unit 220 skips Step S228 and Step S229 to be described below, and performs the process at Step S230 to be described later. Moreover, if it is determined that the final region is not the comparison region A4 (No at Step S227), the arithmetic unit 220 increments the cumulative number, which indicates the number of times of movement of the gaze point P among the regions, by 1 (Step S228), and changes the final region to the comparison region A4 (Step S229). After Step S229, and if it is determined that the gaze point P is not present in the comparison region A4 at Step S226 (No at Step S226), the arithmetic unit 220 performs the processes from Step S230 to be described later.

Thereafter, the arithmetic unit 220 determines whether a time at which replay of the video is completed has come, on the basis of a detection result of the detection timer T1 (Step S230). If the arithmetic unit 220 determines that the time at which replay of the video is completed has not yet come (No at Step S230), the arithmetic unit 220 repeats the processes from Step S206 described above.

If the arithmetic unit 220 determines that the time at which replay of the video is completed has come (Yes at Step S230), the display control unit 202 stops replay of the video (Step S231). After replay of the video is stopped, the evaluation unit 224 calculates the evaluation value ANS2 on the basis of the target presence time data, the target movement frequency data, the final region data, and the target arrival time data that are obtained from processing results as described above (Step S232), and obtains evaluation data on the basis of the evaluation value ANS2. Thereafter, the output control unit 226 outputs the evaluation data obtained by the evaluation unit 224 (Step S233).

As described above, the evaluation apparatus according to the present embodiment includes the display screen 101S that displays an image, the gaze point detection unit 214 that detects a position of a gaze point of a subject who observes the image displayed on the display screen 101S, the display control unit 202 that performs the instruction display operation of displaying, on the display screen 101S, a task target object to be gazed at by the subject and instruction information for instructing the subject to solve a task related to the task target object, the region setting unit 216 that sets, on the display screen 101S, the task region A corresponding to the task target object and the instruction region B corresponding to the instruction information, the determination unit 218 that determines whether the gaze point is present in the task region A and the instruction region B during the instruction display period in which the instruction display operation is performed, on the basis of positional data of the gaze point P, the arithmetic unit 220 that calculates the instruction movement course data indicating the course of movement of the gaze point P during the instruction display period, on the basis of a determination result, and the evaluation unit 224 that obtains evaluation data of the subject on the basis of the instruction movement course data.

Furthermore, the evaluation method according to the present embodiment includes displaying an image on the display screen 101S, detecting a position of a gaze point of a subject who observes the image displayed on the display screen 101S, performing the instruction display operation of displaying, on the display screen 101S, a task target object to be gazed at by the subject and instruction information for instructing the subject to solve a task related to the task target object, setting, on the display screen S101, the task region A corresponding to the task target object and the instruction region B corresponding to the instruction information, determining whether the gaze point is present in the task region A and the instruction region B during the instruction display period in which the instruction display operation is performed, on the basis of positional data of the gaze point P, calculating instruction movement course data indicating the course of movement of the gaze point P during the instruction display period on the basis of a determination result, and obtaining evaluation data of the subject on the basis of the instruction movement course data.

Moreover, the evaluation program according to the present embodiment causes a computer to execute a process of displaying an image on the display screen 101S, a process of detecting a position of a gaze point of a subject who observes the image displayed on the display screen 101S, a process of performing instruction display operation of displaying, on the display screen 101S, a task target object to be gazed at by the subject and instruction information for instructing the subject to solve a task related to the task target object, the task target object, a process of setting, on the display screen S101, the task region A corresponding to the task target object and the instruction region B corresponding to the instruction information, a process of determining whether the gaze point is present in the task region A and the instruction region B during the instruction display period in which the instruction display operation is performed, on the basis of positional data of the gaze point P, a process of calculating instruction movement course data indicating the course of movement of the gaze point P during the instruction display period, on the basis of a determination result, and a process of obtaining evaluation data of the subject on the basis of the instruction movement course data.

According to the present embodiment, the task target object and the instruction information are displayed on the display screen 101S as the instruction display operation. In this case, it is possible to evaluate the subject from the standpoint of whether the subject is attempting to gaze at the task target object indicated by the instruction information after viewing the instruction information displayed on the display screen 101S. Furthermore, it is possible to obtain the evaluation data of the subject on the basis of the course of movement of the gaze point during the display period, so that it is possible to evaluate the subject with high accuracy. Therefore, the evaluation apparatus 100 is able to evaluate the subject with high accuracy.

Moreover, in the evaluation apparatus 100 according to the present embodiment, the instruction movement course data includes the first presence time data that indicates a presence time in which the gaze point P is present in the task region A during the instruction display period, the second presence time data that indicates a presence time in which the gaze point P is present in the instruction region B during the instruction display period, the instruction arrival time data that indicates a time period from a start time of the instruction display period to an arrival time at which the gaze point P arrives at the task region A, and the instruction movement frequency data that indicates the number of times of movement of the position of the gaze point between the task region A and the instruction region B during the instruction display period. Therefore, it is possible to effectively obtain the evaluation data with high accuracy.

Furthermore, in the evaluation apparatus 100 according to the present embodiment, the display control unit 202 displays, on the display screen 101S in the instruction display operation, the instruction information including information for giving an instruction to gaze at a target object that is a correct answer for the task form among a plurality of target objects that are to be displayed on the display screen 101S after the instruction display operation; the display control unit performs, after the instruction display operation, the target display operation of displaying, on the display screen 101S, a plurality of target objects including a specific target object that is a correct answer for the instruction information and comparison target objects that are different from the specific target object; the region setting unit 216 sets, on the display screen 101S, the specific region A1 corresponding to the specific target object and the comparison regions A2 to A4 corresponding to the comparison target objects; the determination unit 218 determines whether the gaze point P is present in the specific region A1 and the comparison regions A2 to A4 during the target display period in which the target display operation is performed; the arithmetic unit 220 calculates the target movement course data indicating the course of movement of the gaze point P during the target display period on the basis of a determination result; and the evaluation unit 224 obtains evaluation data on the basis of the instruction movement course data and the target movement course data. Therefore, it is possible to obtain the evaluation data based on the instruction movement course data and the target movement course data, so that it is possible to obtain the evaluation data with high accuracy.

The technical scope of the present disclosure is not limited to the embodiment as described above, and it is possible to apply modifications appropriately within a scope not departing from the gist of the present disclosure. For example, the example has been described in the above embodiment in which the evaluation apparatus 100 is used as an evaluation apparatus that evaluates possibility of cognitive impairment and brain impairment, but the present disclosure is not limited thereto. For example, the evaluation apparatus 100 may be used as an evaluation apparatus that evaluates a subject who does not have cognitive impairment and brain impairment.

According to the present disclosure, it is possible to provide an evaluation apparatus, an evaluation method, and an evaluation program capable of evaluating cognitive impairment and brain impairment with high accuracy.

What is claimed is:

1. An evaluation apparatus comprising:
a display screen that displays an image;
a gaze point detection unit that detects a position of a gaze point of a subject who observes the display screen;
a display control unit that performs instruction display operation of displaying, on the display screen, a task target object to be gazed at by the subject and instruction information for instructing the subject to solve a task related to the task target object;
a region setting unit that sets, on the display screen, a task region corresponding to the task target object and an instruction region corresponding to the instruction information;
a determination unit that determines whether the gaze point is present in the task region and the instruction region during an instruction display period in which the instruction display operation is performed, on the basis of positional data of the gaze point;
an arithmetic unit that calculates instruction movement course data indicating a course of movement of the gaze point during the instruction display period, on the basis of a determination result; and
an evaluation unit that obtains evaluation data of the subject on the basis of the instruction movement course data, wherein
the display control unit displays, on the display screen in the instruction display operation, instruction information including information for giving an instruction to gaze at a target object that is a correct answer for the task form among a plurality of target objects that are to be displayed on the display screen after the instruction display operation,
the display control unit performs, after the instruction display operation, target display operation of displaying, on the display screen, a plurality of target objects including a specific target object that is a correct answer for the instruction information and comparison target objects that are different from the specific target object,
the region setting unit sets, on the display screen, a specific region corresponding to the specific target object and comparison regions corresponding to the comparison target objects,
the determination unit determines whether the gaze point is present in the specific region and the comparison region during a target display period in which the target display operation is performed,
the arithmetic unit calculates target movement course data indicating a course of movement of the gaze point during the target display period, on the basis of a determination result, and
the evaluation unit obtains evaluation data on the basis of the instruction movement course data and the target movement course data.

2. The evaluation apparatus according to claim 1, wherein the instruction movement course data includes first presence time data that indicates a presence time in which the gaze point is present in the task region during the instruction display period, second presence time data that indicates a presence time in which the gaze point is present in the instruction region during the instruction display period, instruction arrival time data that indicates a time period from a start time of the instruction display period to an arrival time at which the gaze point arrives at the task region, and instruction movement frequency data that indicates number of times of movement of the gaze point between the task region and the instruction region during the instruction display period.

3. An evaluation method comprising:
displaying an image on a display screen;
detecting a position of a gaze point of a subject who observes the display screen;
performing instruction display operation of displaying, on the display screen, a task target object to be gazed at by the subject and instruction information for instructing the subject to solve a task related to the task target object;

setting, on the display screen, a task region corresponding to the task target object and an instruction region corresponding to the instruction information;

determining whether the gaze point is present in the task region and the instruction region during an instruction display period in which the instruction display operation is performed, on the basis of positional data of the gaze point;

calculating instruction movement course data indicating a course of movement of the gaze point during the instruction display period, on the basis of a determination result; and obtaining evaluation data of the subject on the basis of the instruction movement course data, wherein the performing instruction display operation displays, on the display screen in the instruction display operation, instruction information including information for giving an instruction to gaze at a target object that is a correct answer for the task form among a plurality of target objects that are to be displayed on the display screen after the instruction display operation, the performing instruction display operation performs, after the instruction display operation, target display operation of displaying, on the display screen, a plurality of target objects including a specific target object that is a correct answer for the instruction information and comparison target objects that are different from the specific target object, the setting sets, on the display screen, a specific region corresponding to the specific target object and comparison regions corresponding to the comparison target objects, the determining determines whether the gaze point is present in the specific region and the comparison region during a target display period in which the target display operation is performed, the calculating calculates target movement course data indicating a course of movement of the gaze point during the target display period, on the basis of a determination result, and the obtaining obtains evaluation data on the basis of the instruction movement course data and the target movement course data.

4. A non-transitory computer readable recording medium storing therein an evaluation program that causes a computer to execute:

a process of displaying an image on a display screen;

a process of detecting a position of a gaze point of a subject who observes the display screen;

a process of performing instruction display operation of displaying, on the display screen, a task target object to be gazed at by the subject and instruction information for instructing the subject to solve a task related to the task target object;

a process of setting, on the display screen, a task region corresponding to the task target object and an instruction region corresponding to the instruction information;

a process of determining whether the gaze point is present in the task region and the instruction region during an instruction display period in which the instruction display operation is performed, on the basis of positional data of the gaze point;

a process of calculating instruction movement course data indicating a course of movement of the gaze point during the instruction display period, on the basis of a determination result; and a process of obtaining evaluation data of the subject on the basis of the instruction movement course data, wherein the process of performing instruction display operation displays, on the display screen in the instruction display operation, instruction information including information for giving an instruction to gaze at a target object that is a correct answer for the task form among a plurality of target objects that are to be displayed on the display screen after the instruction display operation, the process of performing instruction display operation performs, after the instruction display operation, target display operation of displaying, on the display screen, a plurality of target objects including a specific target object that is a correct answer for the instruction information and comparison target objects that are different from the specific target object, the process of setting sets, on the display screen, a specific region corresponding to the specific target object and comparison regions corresponding to the comparison target objects, the process of determining determines whether the gaze point is present in the specific region and the comparison region during a target display period in which the target display operation is performed, the process of calculating calculates target movement course data indicating a course of movement of the gaze point during the target display period, on the basis of a determination result, and the process of obtaining obtains evaluation data on the basis of the instruction movement course data and the target movement course data.

* * * * *